United States Patent
Yamamoto

(10) Patent No.: US 9,512,118 B2
(45) Date of Patent: *Dec. 6, 2016

(54) CRYSTAL OF FUSED HETEROCYCLIC COMPOUND

(75) Inventor: Katsuhiko Yamamoto, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 222 days.

This patent is subject to a terminal disclaimer.

(21) Appl. No.: 14/125,390

(22) PCT Filed: Jun. 21, 2012

(86) PCT No.: PCT/JP2012/066461
§ 371 (c)(1),
(2), (4) Date: Dec. 11, 2013

(87) PCT Pub. No.: WO2012/176934
PCT Pub. Date: Dec. 27, 2012

(65) Prior Publication Data
US 2014/0113932 A1    Apr. 24, 2014

(30) Foreign Application Priority Data

Jun. 22, 2011  (JP) .................. 2011-138920

(51) Int. Cl.
C07D 471/04    (2006.01)

(52) U.S. Cl.
CPC .................. *C07D 471/04* (2013.01)

(58) Field of Classification Search
CPC .................................. C07D 471/04
See application file for complete search history.

(56) References Cited

U.S. PATENT DOCUMENTS

| 7,618,982 | B2 | 11/2009 | Vanotti et al. | |
|---|---|---|---|---|
| 7,618,984 | B2 | 11/2009 | Yamada et al. | |
| 8,053,438 | B2 | 11/2011 | Allen et al. | |
| 8,217,069 | B2 | 7/2012 | Yonekubo et al. | |
| 8,247,418 | B2 | 8/2012 | Allen et al. | |
| 8,318,718 | B2 | 11/2012 | Allen et al. | |
| 8,329,700 | B2 | 12/2012 | Allen et al. | |
| 8,563,575 | B2 * | 10/2013 | Taniguchi | A61K 31/4355 514/301 |
| 8,846,713 | B2 * | 9/2014 | Taniguchi | A61K 31/4355 514/303 |
| 8,940,758 | B2 * | 1/2015 | Taniguchi | A61K 31/4355 514/301 |
| 9,226,921 | B2 * | 1/2016 | Taniguchi | A61K 31/4355 |
| 2007/0142415 | A1 | 6/2007 | Vanotti et al. | |

(Continued)

FOREIGN PATENT DOCUMENTS

| WO | 2007/026664 | 3/2007 |
|---|---|---|
| WO | 2007/034035 | 3/2007 |

(Continued)

OTHER PUBLICATIONS

Tsuang et al. Am J Psychiatry 2000; 157:1041-1050.*

(Continued)

*Primary Examiner* — Matthew Coughlin
(74) *Attorney, Agent, or Firm* — Wenderoth, Lind & Ponack, L.L.P.

(57) ABSTRACT

The present invention relates to a crystal of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one useful as a prophylactic or therapeutic agent for schizophrenia and the like, which shows an X-ray powder diffraction pattern having characteristic peaks at interplaner spacings (d) of 13.59 plus or minus 0.2 and 6.76 plus or minus 0.2 Angstroms in powder X-ray diffraction.

4 Claims, 5 Drawing Sheets

(56) References Cited

U.S. PATENT DOCUMENTS

| | | |
|---|---|---|
| 2007/0179127 A1 | 8/2007 | Yamada et al. |
| 2008/0090834 A1 | 4/2008 | Hoover et al. |
| 2009/0023735 A1 | 1/2009 | Heino et al. |
| 2011/0098288 A1 | 4/2011 | Major et al. |
| 2012/0277209 A1 | 11/2012 | Allen et al. |
| 2013/0079325 A1 | 3/2013 | Allen et al. |
| 2013/0137675 A1 | 5/2013 | Taniguchi et al. |
| 2013/0172292 A1 | 7/2013 | Raker et al. |
| 2013/0172328 A1 | 7/2013 | Taniguchi et al. |

FOREIGN PATENT DOCUMENTS

| | | |
|---|---|---|
| WO | 2007/071621 | 6/2007 |
| WO | 2008/004117 | 1/2008 |
| WO | 2008/129994 | 10/2008 |
| WO | 2009/112490 | 9/2009 |
| WO | 2010/057121 | 5/2010 |
| WO | 2010/057126 | 5/2010 |
| WO | 2010/126002 | 11/2010 |
| WO | 2011/163355 | 12/2011 |
| WO | 2012/018909 | 2/2012 |
| WO | 2012/020780 | 2/2012 |
| WO | 2012/124782 | 9/2012 |

OTHER PUBLICATIONS

Mayo Clinic, Schizophrenia Prevention, obtained from http://www.mayoclinic.org/diseases-conditions/schizophrenia/basics/prevention/con-20021077 on Sep. 29, 2015.*
International Search Report issued Sep. 20, 2012 in International (PCT) Application No. PCT/JP2012/066461.

* cited by examiner

CRYSTAL OF FUSED HETEROCYCLIC COMPOUND

TECHNICAL FIELD OF THE INVENTION

The present invention relates to a crystal of a fused heterocyclic compound, which has a superior phosphodiesterase 10A inhibitory action, and is useful as an agent for the treatment or prophylaxis of schizophrenia etc., and the like.

BACKGROUND OF THE INVENTION

Phosphodiesterases (PDEs) are a superfamily of enzymes encoded by 21 genes and subdivided into 11 distinct families according to structural and functional properties. These enzymes metabolically inactivate the ubiquitous intracellular second messengers, cyclic adenosine monophosphate (cAMP) and cyclic guanosine monophosphate (cGMP); PDEs selectively catalyze the hydrolysis of the 3'-ester bond, forming the inactive 5'-monophosphate. On the basis of substrate specificity, the PDE families can be further classified into three groups: i) the cAMP-PDEs (PDE4, PDE7, PDE8), ii) the cGMP-PDEs (PDE5, PDE6 and PDE9), and iii) the dual-substrate PDEs (PDE1, PDE2, PDE3, PDE10 and PDE11).

The cAMP and cGMP are involved in the regulation of virtually every physiological process such as pro-inflammatory mediator production and action, ion channel function, muscle relaxation, learning and memory formation, differentiation, apoptosis, lipogenesis, glycogenolysis and gluconeogenesis. Especially, in neurons, these second messengers have important role in the regulation of synaptic transmission as well as in neuronal differentiation and survival (non-patent document 1). Regulation of these processes by cAMP and cGMP are accompanied by activation of protein kinase A (PKA) and protein kinase G (PKG), which in turn phosphorylate a variety of substrates, including transcription factors, ion channels and receptors that regulate a variety of physiological processes. Intracellular cAMP and cGMP concentrations seem to be temporally, Spatially, and functionally compartmentalized by regulation of adenyl and guanyl cyclases in response to extracellular signaling and their degradation by PDEs (non-patent document 2). PDEs provide the only means of degrading the cyclic nucleotides cAMP and cGMP in cells, thus PDEs play an essential role in cyclic nucleotide signal transduction. Thereby, PDEs could be promising targets for various therapeutic drugs.

Phosphodiesterase 10A (PDE10A) was discovered in 1999 (non-patent documents 3-5). Expression studies have shown that PDE10A has the most restricted distribution within the all known PDE families; the PDE10A mRNA is highly expressed only in brain and testes (non-patent documents 6 and 7). In the brain, mRNA and protein of PDE10A are highly enriched in medium spiny neurons (MSNs) of the striatum (non-patent documents 8 and 9). MSNs are classified into two groups: the MSN that express $D_1$ dopamine receptors responsible for a direct (striatonigral) pathway and the MSN that express $D_2$ dopamine receptors responsible for an indirect (striatopallidal) pathway. The function of direct pathway is to plan and execution, while indirect pathway is to act as a brake on behavioral activation. As PDE10A is expressed in both MSNs, PDE10A inhibitors could activate both of these pathways. The antipsychotic efficacy of current medications, $D_2$ or $D_2$/5-$HT_{2A}$ antagonists, mainly derives from their activation of the indirect pathway in the striatum. As PDE10A inhibitors are able to activate this pathway, this suggests that PDE10A inhibitors are promising as antipsychotic drugs. The excessive $D_2$ receptor antagonism in the brain by $D_2$ antagonists causes problems of extrapyramidal side effects and hyperprolactinaemia. However the expression of PDE10A is limited to these striatal pathways in the brain, thus side effects by PDE10A inhibitors were expected to be weaker compared with current $D_2$ antagonists. Regarding hyperprolactinaemia, PDE10A inhibitors would produce no prolactin elevation due to lack of $D_2$ receptor antagonism in the pituitary. Moreover, the presence of PDE10A in a direct pathway makes it likely that PDE10A inhibitors will have some advantage over current $D_2$ antagonists; the direct pathway is thought to promote desired action, and activation of this pathway by PDE10A inhibitors may counteract extrapyramidal symptoms induced by excessive $D_2$ receptor antagonism. In addition, activation of this pathway could facilitate striatal-thalamic outflow, promoting the execution of procedural strategies. Furthermore, enhancement of second messenger levels without blockade of dopamine and/or other neurotransmitter receptors may also provide therapeutic advantages with fewer adverse side-effects compared with current antipsychotics (e.g., hyperprolactinaemia and weight gain). This unique distribution and function in the brain indicates that PDE10A represents an important new target for the treatment of neurological and psychiatric disorders, in particular psychotic disorders like schizophrenia.

Patent document 1 describes, as a phosphodiesterase (PDE) 10 inhibitor, a compound represented by the formula:

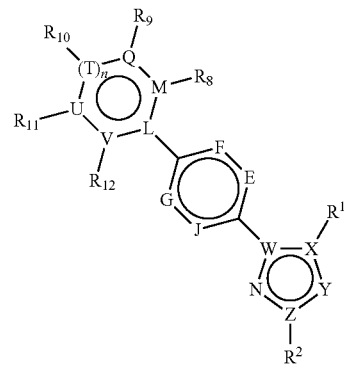

wherein each symbol is as defined in patent document 1, and the following compounds:

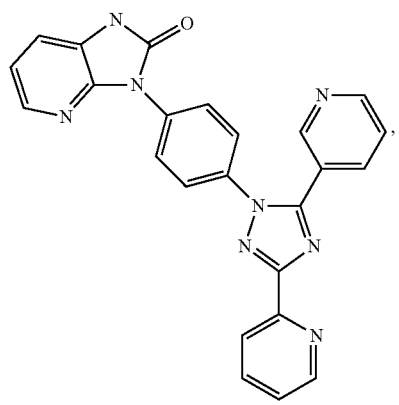

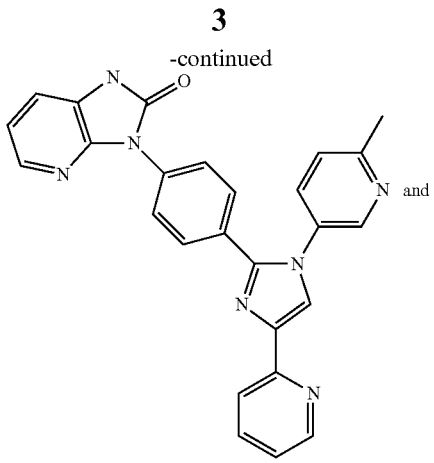

and

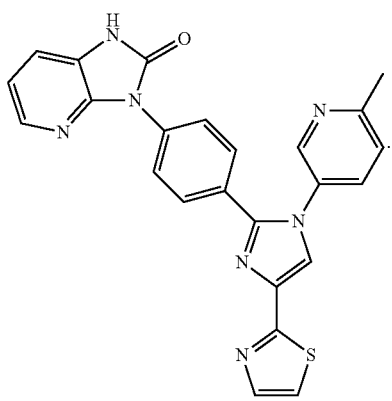

Patent document 2 describes, as a phosphodiesterase (PDE) 10 inhibitor, a compound represented by the formula:

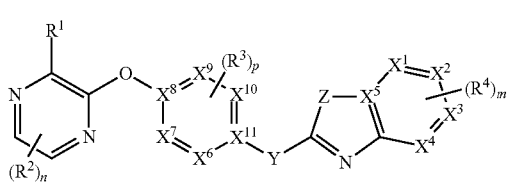

wherein each symbol is as defined in patent document 2, and the following compounds:

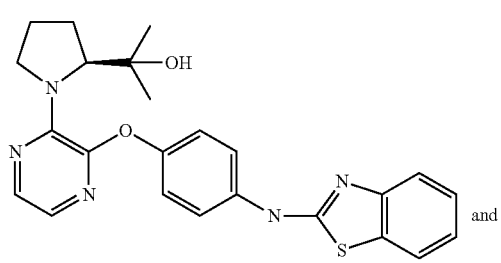

and

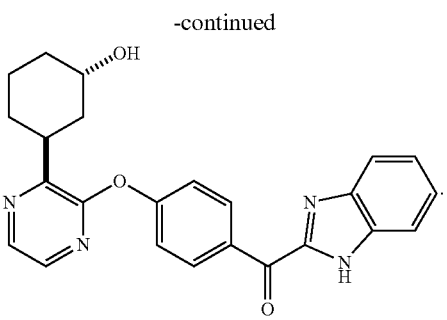

Patent document 3 describes, as a phosphodiesterase (PDE) 10 inhibitor, a compound represented by the formula:

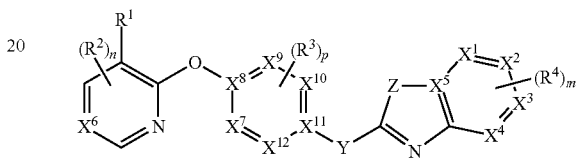

wherein each symbol is as defined in patent document 3, and the following compounds:

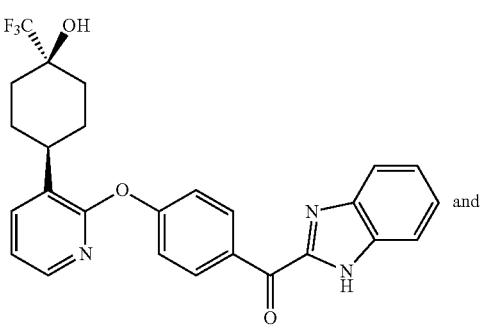

and

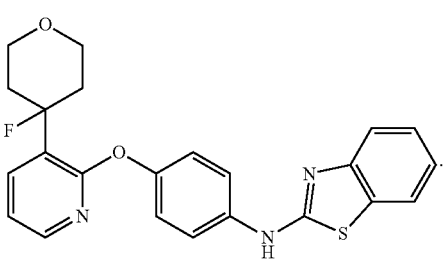

Patent document 4 describes, as a phosphodiesterase (PDE) 10 inhibitor, a compound represented by the formula:

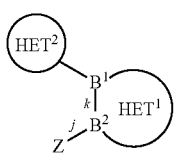

I wherein Z is

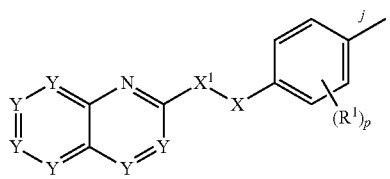

wherein each symbol is as defined in patent document 4.

Patent document 5 describes, as a phosphodiesterase (PDE) 10 inhibitor, a compound represented by the formula:

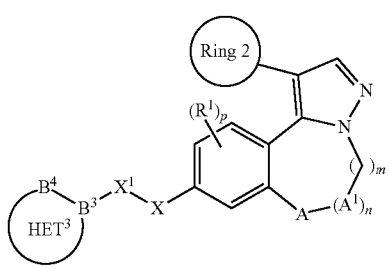

(I)

wherein each symbol is as defined in patent document 5.

Patent document 6 describes, as a phosphodiesterase (PDE) 10 inhibitor, a compound represented by the formula:

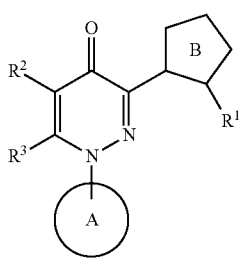

wherein each symbol is as defined in patent document 6.

DOCUMENT LIST

Patent Documents patent document 1: WO2008/004117
patent document 2: WO2010/057121
patent document 3: WO2010/057126
patent document 4: WO2006/072828
patent document 5: WO2008/001182
patent document 6: WO2010/090737

Non-Patent Documents non-patent document 1: Nat. Rev. Drug Discov. 2006, vol. 5, p. 660-670
non-patent document 2: Circ. Res. 2007, vol. 100(7), p. 950-966
non-patent document 3: Proc. Natl. Acad. Sci. USA, 1999, vol. 96, p. 8991-8996
non-patent document 4: J. Biol. Chem. 1999, vol. 274, p. 18438-18445
non-patent document 5: Gene, 1999, vol. 234, p. 109-117
non-patent document 6: Eur. J. Biochem. 1999, vol. 266, p. 1118-1127
non-patent document 7: J. Biol. Chem. 1999, vol. 274, p. 18438-18445
non-patent document 8: Eur. J. Biochem. 1999, vol. 266, p. 1118-1127
non-patent document 9: Brain Res. 2003, vol. 985, p. 113-126

SUMMARY OF THE INVENTION

Problems to be Solved by the Invention

The development of a compound having a superior PDE10A inhibitory action, which is useful as an agent for the treatment or prophylaxis of schizophrenia etc. and the like, and has properties superior in the stability, has been desired.

Means of Solving the Problems

The present inventors have conducted intensive studies in an attempt to solve the aforementioned problems and successfully obtained 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one as a crystal which is thermodynamically, chemically and physically highly stable. In addition, they have found that the crystal has a superior PDE10A inhibitory action, and is sufficiently satisfactory as a medicament for the treatment or prophylaxis of schizophrenia and the like. They have completed the present invention based on these findings.

Accordingly, the present invention relates to

[1] a crystal of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one showing an X-ray powder diffraction pattern having characteristic peaks at interplaner spacings (d) of 13.59±0.2 and 6.76±0.2 Angstroms in powder X-ray diffraction (hereinafter sometimes to be referred to as the crystal of the present invention);

[2] the crystal of the above-mentioned [1], which shows an X-ray powder diffraction pattern having further characteristic peaks at interplaner spacings (d) of 9.22±0.2, 7.88±0.2, 6.21±0.2, 6.13±0.2, 5.73±0.2, 4.64±0.2, 3.79±0.2 and 3.75±0.2 Angstroms in powder X-ray diffraction;

[3] the crystal of the above-mentioned [2], which shows an X-ray powder diffraction pattern having further characteristic peaks at interplaner spacings (d) of 7.48±0.2, 5.24±0.2, 5.13±0.2, 4.27±0.2, 4.16±0.2, 4.06±0.2, 3.99±0.2, 3.93±0.2, 3.60±0.2, 3.41±0.2, 3.16±0.2, 3.10±0.2, 3.06±0.2, 2.89±0.2, 2.83±0.2, 2.73±0.2 and 2.58±0.2 Angstroms in powder X-ray diffraction;

[4] the crystal of the above-mentioned [1], which shows an initial temperature of about 222-about 224° C. of an endothermic behavior caused by melting in DSC measurement (temperature increase rate 5° C./min);

[5] a medicament comprising the crystal of the above-mentioned [1];

[6] the medicament of the above-mentioned [5], which is a phosphodiesterase 10A inhibitor;

[7] the medicament of the above-mentioned [5], which is a prophylactic or therapeutic agent for schizophrenia;

[8] a method of preventing or treating schizophrenia in a mammal, comprising administering an effective amount of the crystal of the above-mentioned [1] to the mammal;

[9] use of the crystal of the above-mentioned [1] for the production of a prophylactic or therapeutic drug for schizophrenia;

[10] the crystal of the above-mentioned [1] for use for the prophylaxis or treatment of schizophrenia; and the like.

Effect of the Invention

Since the crystal of the present invention shows a superior PDE10A inhibitory action, is low toxic and is superior in stability, it is useful as a pharmaceutical product.

Figure 1:
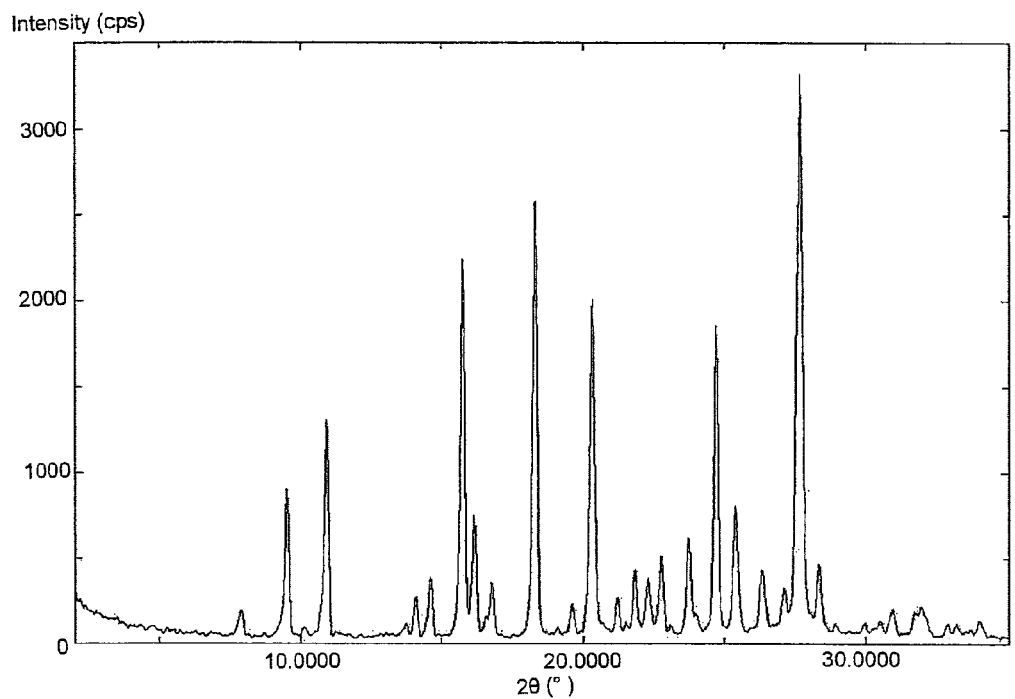
FIG. 1 shows a powder X-ray diffraction pattern of the crystal of Reference Example 1-1.

DESCRIPTION OF EMBODIMENTS (Detailed Description of the Invention)

The crystal of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one in the present invention may be a solvate such as hydrate and the like, or a non-solvate such as nonhydrate (anhydrate) and the like.

Examples of the "hydrate" include 0.5 hydrate to 5.0 hydrate. Among these, 0.5 hydrate, 1.0 hydrate, 1.5 hydrate, 2.0 hydrate and 2.5 hydrate are preferable. Particularly preferred are 0.5 hydrate, 1.0 hydrate and 1.5 hydrate. In addition, the aforementioned "hydrate" may also be a "variable hydrate" containing a variable amount of water in the crystal structure according to the humidity environment. The water content of the variable hydrate varies within the range of about 4.0-about 14.5 wt %.

1-Ethyl-7-methyl-3-{4-[(3-methyl-3H-imidazo[4,5-b]pyridin-2-yl)oxy]phenyl}-1,3-dihydro-2H-imidazo[4,5-b]pyridin-2-one in the present invention may also be a deuteride thereof.

In addition, the crystal of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one in the present invention may also be a solvate other than a hydrate.

Examples of the solvate crystal of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one include alcohol solvate crystals such as methanol solvate crystal, ethanol solvate crystal and the like (preferably $C_{1-6}$ alcohol solvate crystal), organic solvent hydrate crystal to which water and organic solvent are added (e.g., alcohol hydrate crystals such as methanol hydrate, ethanol hydrate, etc., preferably $C_{1-6}$ alcohol hydrate crystal) and the like.

The crystal of the present invention can be produced by crystal transformation of amorphous 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one or other crystals (including hydrate crystal) of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one.

The crystal transformation is a phenomenon where a crystal structure changes when the temperature or pressure exceeds a certain level.

As the "crystal transformation method", a method known per se can be mentioned and, for example, crystallization from a solution (e.g., concentration method, slow cooling method, reaction method (diffusion method, electrolysis method), hydrothermal growth method, flux method and the like), crystallization from the above (e.g., a gasification method (sealed tube method, gas stream method), a gas phase reaction method, a chemical transportation method), crystallization from molten form (e.g., a normal freezing method (pulling-up method, temperature gradient method, Bridgman method), a zone melting method (zone leveling method, float zone method), a special growth method (VLS method, liquid phase epitaxis method), a transpiration method (a method including dissolving a crystal in a solvent, filtering and evaporating the solvent under ambient conditions), a slurry method (a method including adding a crystal to a solvent such that an excess solid remains to give a suspension, stirring the suspension at ambient temperature or under heating or cooling, and collecting the solid), drying under reduced pressure, grinding, pulverization, pressurization and the like can be mentioned.

To obtain the crystal of the present invention, a slurry method is preferable from among the above.

For analyzing the crystal obtained, X-ray diffraction crystallographic analysis is commonly used. In addition, crystal orientation can also be determined by a mechanical method, an optical method (e.g., FT-Raman spectrum, solid-state NMR spectrum), etc. In addition, crystal thermoanalysis (Differential Scanning calorimetry (DSC)), infrared absorption spectrum analysis (KBr) and the like can also be performed according to conventional methods.

The peak of the spectrum obtained by the above-mentioned analysis method inevitably contains a certain measurement error by its nature. A crystal with a spectrum peak within the error range is also encompassed in the crystal of the present invention. For example, "±0.2" or "±0.1" in the interplanar spacing (d) of powder X-ray diffraction means that the error is tolerable.

The crystal of the present invention produced by the aforementioned method is a novel crystal showing an X-ray powder diffraction pattern having characteristic peaks at interplanar spacings (d) of 13.59±0.2 and 6.76±0.2 Angstroms, by powder X-ray diffraction, and is preferably a crystal of non-solvate (e.g., anhydrate).

The crystal of the present invention is preferably a crystal showing an X-ray powder diffraction pattern having characteristic peaks at interplanar spacings (d) of 13.59±0.2, 9.22±0.2, 7.88±0.2, 6.76±0.2, 6.21±0.2, 6.13±0.2, 5.73±0.2, 4.64±0.2, 3.79±0.2 and 3.75±0.2 Angstroms, by powder X-ray diffraction, and is preferably a crystal of non-solvate (e.g., anhydrate).

The crystal of the present invention is more preferably a crystal showing an X-ray powder diffraction pattern having characteristic peaks at interplanar spacings (d) of 13.59±0.2, 9.22±0.2, 7.88±0.2, 7.48±0.2, 6.76±0.2, 6.21±0.2, 6.13±0.2, 5.73±0.2, 5.24±0.2, 5.13±0.2, 4.64±0.2, 4.27±0.2, 4.16±0.2, 3.99±0.2, 3.93±0.2, 3.79±0.2, 3.75±0.2, 3.60±0.2, 3.41±0.2, 2.89±0.2, 2.73±0.2 and 2.58±0.2 Angstroms, by powder X-ray diffraction, and is preferably a crystal of non-solvate (e.g., anhydrate).

The crystal of the present invention is further more preferably a crystal showing an X-ray powder diffraction pattern having characteristic peaks at interplanar spacings (d) of 13.59±0.2, 9.22±0.2, 7.88±0.2, 7.48±0.2, 6.76±0.2, 6.21±0.2, 6.13±0.2, 5.73±0.2, 5.24±0.2, 5.13±0.2, 4.64±0.2, 4.27±0.2, 4.16±0.2, 4.06±0.2, 3.99±0.2, 3.93±0.2, 3.79±0.2, 3.75±0.2, 3.60±0.2, 3.41±0.2, 3.16±0.2, 3.10±0.2, 3.06±0.2, 2.89±0.2, 2.83±0.2, 2.73±0.2 and 2.58±0.2 Angstroms, by powder X-ray diffraction, and is preferably a crystal of non-solvate (e.g., anhydrate).

As another embodiment, the crystal of the present invention produced by the aforementioned method is a novel crystal showing an X-ray powder diffraction pattern having characteristic peaks at interplanar spacings (d) of 13.59±0.1 and 6.76±0.1 Angstroms, by powder X-ray diffraction, and is preferably a crystal of non-solvate (e.g., anhydrate).

The crystal of the present invention is preferably a crystal showing an X-ray powder diffraction pattern having characteristic peaks at interplanar spacings (d) of 13.59±0.1, 9.22±0.1, 7.88±0.1, 6.76±0.1, 6.21±0.1, 6.13±0.1, 5.73±0.1, 4.64±0.1, 3.79±0.1 and 3.75±0.1 Angstroms, by powder X-ray diffraction, and is preferably a crystal of non-solvate (e.g., anhydrate).

The crystal of the present invention is more preferably a crystal showing an X-ray powder diffraction pattern having characteristic peaks at interplanar spacings (d) of 13.59±0.1, 9.22±0.1, 7.88±0.1, 7.48±0.1, 6.76±0.1, 6.21±0.1, 6.13±0.1, 5.73±0.1, 5.24±0.1, 5.13±0.1, 4.64±0.1, 4.27±0.1, 4.16±0.1, 3.99±0.1, 3.93±0.1, 3.79±0.1, 3.75±0.1, 3.60±0.1, 3.41±0.1, 2.89±0.1, 2.73±0.1 and 2.58±0.1 Angstroms, by powder X-ray diffraction, and is preferably a crystal of non-solvate (e.g., anhydrate).

The crystal of the present invention is further more preferably a crystal showing an X-ray powder diffraction pattern having characteristic peaks at interplanar spacings (d) of 13.59±0.1, 9.22±0.1, 7.88±0.1, 7.48±0.1, 6.76±0.1, 6.21±0.1, 6.13±0.1, 5.73±0.1, 5.24±0.1, 5.13±0.1, 4.64±0.1, 4.27±0.1, 4.16±0.1, 4.06±0.1, 3.99±0.1, 3.93±0.1, 3.79±0.1, 3.75±0.1, 3.60±0.1, 3.41±0.1, 3.16±0.1, 3.10±0.1, 3.06±0.1, 2.89±0.1, 2.83±0.1, 2.73±0.1 and 2.58±0.1 Angstroms, by powder X-ray diffraction, and is preferably a crystal of non-solvate (e.g., anhydrate). The crystal of the present invention is preferably anhydrous crystal.

The crystal of the present invention shows an initial temperature of about 222-about 224° C., preferably about 223° C., of an endothermic behavior caused by melting in DSC measurement under the conditions of temperature increase rate 5° C./min, wherein the "about" here means±1° C.

The crystal of the present invention shows a peak temperature of about 223° C.-about 225° C., preferably about 224° C., of an endothermic behavior caused by melting in DSC measurement under conditions of temperature increase rate 5° C./min, wherein the "about" here means±1° C. The peak temperature of an endothermic behavior is higher than the initial temperature.

The crystal of the present invention does not have two or more endothermic behaviors between room temperature and about 240° C. (it has only a peak of an endothermic behavior caused by one melting) in DSC measurement under conditions of temperature increase rate 5° C./min, wherein the "about" here means±1° C.

The purity of the crystal of the present invention is about 95%-100%, preferably about 97%-100%, more preferably about 99%-100%.

The thus-obtained crystal of the present invention has a superior PDE10A inhibitory action, is low toxic and is useful as a pharmaceutical product. Moreover, since the crystal of the present invention is superior in stability, it can be handled easily and can be processed into a solid pharmaceutical composition with good reproducibility.

The crystal of the present invention is useful for the prophylaxis and/or treatment of, for example, the following diseases or symptoms, in mammals (e.g., humans, cows, horses, dogs, cats, monkeys, mice, rats, etc. particularly humans): psychotic disorder (e.g., brief psychotic disorder, shared psychotic disorder);

psychosis induced by alcohol, amphetamine, cannabis, cocaine, hallucinogens, obesity, inhalants, opioids, or phencyclidine;

delusional disorder;

anxiety disorder;

movement disorder;

mood disorder;

major depressive disorder;

a major depressive disorder superimposed on a psychotic disorder comprising a delusional disorder or schizophrenia;

major depressive episode of the mild, moderate or severe type;

manic or mixed mood episode;

hypomanic mood episode;

depressive episode with atypical features;

depressive episode with melancholic features;

depressive episode with catatonic features;

mood episode with postpartum onset;

post-stroke depression;

dysthymic disorder;

minor depressive disorder;

autism;

drug addiction;

neurodegenerative disorder;

neurodegeneration associated with cerebral trauma;

neurodegeneration associated with stroke;

neurodegeneration associated with cerebral infarct;

hypoglycemia-induced neurodegeneration;

neurodegeneration associated with epileptic seizure;

neurodegeneration associated with neurotoxin poisoning;

multi-system atrophy;

Alzheimer's disease;

dementia;

multi-infarct dementia;

alcoholic dementia or other drug-related dementia;

dementia associated with intracranial tumors or cerebral trauma;

dementia associated with Huntington's disease or Parkinson's disease;

AIDS-related dementia;

frontotemporal dementia;

delirium;

amnestic disorder;

post-traumatic stress disorder;

mental retardation;

learning disorder (e.g., reading disorder, mathematics disorder, or a disorder of written expression);

attention-deficit/hyperactivity disorder;

age-related cognitive decline;

premenstrual dysphoric disorder;

post-psychotic depressive disorder of schizophrenia;

bipolar disorders comprising bipolar I disorder and bipolar II disorder;
cyclothymic disorder;
Parkinson's disease;
Huntington's disease;
paranoid;
schizophrenia (e.g., paranoid schizophrenia, disorganized schizophrenia, catatonic schizophrenia, undifferentiated schizophrenia, residual schizophrenia);
schizophreniform disorder;
schizoaffective disorder of the delusional type or the depressive type;
personality disorder of the paranoid type;
personality disorder of the schizoid type;
obesity;
metabolic syndrome;
non-insulin dependent diabetes mellitus (NIDDM);
glucose intolerance;
and the like, particularly for the prophylaxis and/or treatment of schizophrenia.

The crystal of the present invention is of low toxicity and can be safely administered orally or non-orally (e.g., topical, rectal and intravenous administration, etc.), as such or in the form of pharmaceutical compositions formulated with a pharmacologically acceptable carrier, e.g., tablets (including sugar-coated tablets and film-coated tablets), powders, granules, capsules (including soft capsules), orally disintegrating tablets, orally disintegrating films, liquids, injectable preparations, suppositories, sustained-release preparations and patches, in accordance with a commonly known method.

The content of the crystal of the present invention in the pharmaceutical composition is about 0.01 to 100% by weight of the entire composition. While the dose varies depending on the subject of administration, administration route, target disease, symptom and the like, for example, for oral administration to a patient with schizophrenia (adult, about 60 kg body weight), a single dose is generally within the range of about 0.1-about 20 mg/kg body weight, preferably about 0.2-about 10 mg/kg body weight, more preferably about 0.5-about 10 mg/kg body weight. Such dose is preferably administered one—several times (e.g., 3 times) per day.

Pharmacologically acceptable carriers that may be used to produce the pharmaceutical composition of the present invention include various organic or inorganic carrier substances in common use as pharmaceutical materials, including excipients, lubricants, binders, disintegrants, water-soluble polymers and basic inorganic salts for solid preparations; and solvents, solubilizing agents, suspending agents, isotonizing agents, buffers and soothing agents for liquid preparations. Other ordinary pharmaceutical additives such as preservatives, antioxidants, colorants, sweetening agents, souring agents, bubbling agents, flavorings and the like may also be used as necessary.

Such "excipients" include, for example, lactose, sucrose, D-mannitol, starch, cornstarch, crystalline cellulose, light anhydrous silicic acid, titanium oxide and the like.

Such "lubricants" include, for example, magnesium stearate, sucrose ester of fatty acids, polyethylene glycol, talc and stearic acid.

Such "binders" include, for example, hydroxypropyl cellulose, hydroxypropyl methylcellulose, crystalline cellulose, α-starch, polyvinylpyrrolidone, gum arabic powder, gelatin, pullulan, low-substituted hydroxypropyl cellulose and the like.

Such "disintegrants" include (1) crospovidone, (2) what is called super-disintegrants such as croscarmellose sodium (FMC-Asahi Chemical) and carmellose calcium (GOTOKU CHEMICAL CO., LTD.), (3) sodium carboxymethyl starch (e.g., product of Matsutani Chemical), (4) low-substituted hydroxypropyl cellulose (e.g.; product of Shin-Etsu Chemical), (5) cornstarch, and so forth. Said "crospovidone" may be any crosslinked polymer having the chemical name 1-ethenyl-2-pyrrolidinone homopolymer, including polyvinylpolypyrrolidone (PVPP) and 1-vinyl-2-pyrrolidinone homopolymer, and is exemplified by Colidon CL (produced by BASF), Polyplasdon XL (produced by ISP), Polyplasdon XL-10 (produced by ISP), Polyplasdon INF-10 (produced by ISP) and the like.

Such "water-soluble polymers" include, for example, ethanol-soluble water-soluble polymers and the like [e.g., cellulose derivatives such as hydroxypropyl cellulose (hereinafter also referred to as HPC), polyvinylpyrrolidone] and ethanol-insoluble water-soluble polymers [e.g., cellulose derivatives such as hydroxypropyl methylcellulose (hereinafter also referred to as HPMC), methyl cellulose and carboxymethyl cellulose sodium, sodium polyacrylate, polyvinyl alcohol, sodium alginate, guar gum and the like].

Such "basic inorganic salts" include, for example, basic inorganic salts of sodium, potassium, magnesium and/or calcium. Preferred are basic inorganic salts of magnesium and/or calcium. More preferred are basic inorganic salts of magnesium. Such basic inorganic salts of sodium include, for example, sodium carbonate, sodium hydrogen carbonate, disodium hydrogenphosphate, etc. Such basic inorganic salts of potassium include, for example, potassium carbonate, potassium hydrogen carbonate, etc. Such basic inorganic salts of magnesium include, for example, heavy magnesium carbonate, magnesium carbonate, magnesium oxide, magnesium hydroxide, magnesium aluminometasilicate, magnesium silicate, magnesium aluminate, synthetic hydrotalcite [$Mg_6Al_2(OH)_{16}.CO_3.4H_2O$] and aluminum magnesium hydroxide. Among others, preferred is heavy magnesium carbonate, magnesium carbonate, magnesium oxide, magnesium hydroxide, etc. Such basic inorganic salts of calcium include, for example, precipitated calcium carbonate, calcium hydroxide, etc.

Such "solvents" include, for example, water for injection, alcohol, propylene glycol, macrogol, sesame oil, corn oil, olive oil, etc.

Such "solubilizing agents" include, for example, polyethylene glycol, propylene glycol, D-mannitol, benzylbenzoate, ethanol, tris-aminomethane, cholesterol, triethanolamine, sodium carbonate, sodium citrate and the like.

Such "suspending agents" include, for example, surfactants such as stearyl triethanolamine, sodium lauryl sulfate, lauryl aminopropionic acid, lecithin, benzalkonium chloride, benzethonium chloride, glycerol monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropyl cellulose etc. and the like.

Such "isotonizing agents" include, for example, glucose, D-sorbitol, sodium chloride, glycerol, D-mannitol and the like.

Such "buffers" include, for example, buffer solutions of phosphates, acetates, carbonates, citrates, etc.

Such "soothing agents" include, for example, benzyl alcohol and the like.

Such "preservatives" include, for example, p-oxybenzoic acid esters, chlorobutanol, benzyl alcohol, phenethyl alcohol, dehydroacetic acid, sorbic acid and the like.

Such "antioxidants" include, for example, sulfites, ascorbic acid, α-tocopherol and the like.

Such "colorants" include, for example, food colors such as Food Color Yellow No. 5, Food Color Red No. 2 and Food Color Blue No. 2; and food lake colors, red ferric oxide and the like.

Such "sweetening agents" include, for example, saccharin sodium, dipotassium glycyrrhetinate, aspartame, stevia, thaumatin and the like.

Such "souring agents" include, for example, citric acid (anhydrous citric acid), tartaric acid, malic acid and the like.

Such "bubbling agents" include, for example, sodium bicarbonate and the like.

Such "flavorings" may be synthetic substances or naturally occurring substances, and include, for example, lemon, lime, orange, menthol, strawberry and the like.

The crystal of the present invention may be prepared as a preparation for oral administration in accordance with a commonly known method, by, for example, compression-shaping it in the presence of an excipient, a disintegrant, a binder, a lubricant, or the like, and subsequently coating it as necessary by a commonly known method for the purpose of taste masking, enteric dissolution or sustained release. For an enteric preparation, an intermediate layer may be provided by a commonly known method between the enteric layer and the drug-containing layer for the purpose of separation of the two layers.

For preparing the crystal of the present invention as an orally disintegrating tablet, available methods include, for example, a method in which a core containing crystalline cellulose and lactose is coated with the crystal of the present invention and a basic inorganic salt, and is further coated with a coating layer containing a water-soluble polymer to give a composition, which is coated with an enteric coating layer containing polyethylene glycol, further coated with an enteric coating layer containing triethyl citrate, still further coated with an enteric coating layer containing polyethylene glycol, and still yet further coated with mannitol to give fine granules, which are mixed with additives and shaped, and the like. The above-mentioned "enteric coating layer" includes, for example, aqueous enteric polymer substrates such as cellulose acetate phthalate (CAP), hydroxypropyl methylcellulose phthalate, hydroxymethyl cellulose acetate succinate, methacrylic acid copolymers [e.g., Eudragit L30D-55 (trade name; produced by Rohm), Colicoat MAE30DP (trade name; produced by BASF), Polykid PA30 (trade name; produced by San-yo Chemical) and the like], carboxymethyl ethyl cellulose, shellac and the like; sustained-release substrates such as methacrylic acid copolymers [e.g., Eudragit NE30D (trade name), Eudragit RL30D (trade name), Eudragit RS30D (trade name), etc.] and the like; water-soluble polymers; plasticizers such as triethyl citrate, polyethylene glycol, acetylated monoglycerides, triacetine, castor oil and the like; and mixtures thereof, and the like. The above-mentioned "additive" includes, for example, water-soluble sugar alcohols (e.g., sorbitol, mannitol, maltitol, reduced starch saccharides, xylitol, reduced palatinose, erythritol, etc.), crystalline cellulose [e.g., Ceolas KG 801, Avicel PH 101, Avicel PH 102, Avicel PH 301, Avicel PH 302, Avicel RC-591 (crystalline cellulose carmellose sodium) and the like], low-substituted hydroxypropyl cellulose [e.g., LH-22, LH-32, LH-23, LH-33 (Shin-Etsu Chemical) and mixtures thereof and the like] and the like; binders, souring agents, bubbling agents, sweetening agents, flavorings, lubricants, colorants, stabilizers, excipients, disintegrants etc. are also used.

The crystal of the present invention can be administered as the sole active agent or in combination with other medicaments such as other agents used in the treatment of psychosis, especially schizophrenia and bipolar disorder, obsessive-compulsive disorder, major depression, Parkinson's disease, Alzheimer's disease, cognitive impairment and/or memory loss [e.g., nicotinic $\alpha 7$ agonists, nicotinic $\alpha 7$ partial agonists, nicotinic $\alpha 7$ positive allosteric modulators, PDE2 inhibitors, PDE4 inhibitors, PDE5 inhibitors, other PDE inhibitors, calcium channel blockers, muscarinic m1 and m2 modulators, adenosine receptor modulators, ampakines, Glycine transporter 1 inhibitors, NMDA-R modulators, mGluR modulators, dopamine modulators, serotonin modulators, selective serotonin reuptake inhibitors, serotonin and norepinephrine reuptake inhibitors, norepinephrine and dopamine reuptake inhibitors, triple reuptake inhibitors, cannabinoid modulators, and cholinesterase inhibitors (e.g., donepezil, rivastigmine, and galanthamine)]. In such combinations, each active ingredient can be administered either in accordance with their usual dosage range or a dose below their usual dosage range, and can be administered either simultaneously or sequentially.

Drugs suitable in combination with the crystal of the present invention include, but are not limited to, other suitable schizophrenia drugs such as Haloperidol, Clozapine, Olanzapine, Risperidone, Aripiprazole, Ziprasidone, Paliperidone, and Quetiapine fumarate; bipolar disorder drugs, including, but not limited to, Lithium, Olanzapine, Aripiprazole, and Valproic acid; Parkinson's disease drugs, including, but not limited to, Levodopa, Bromocriptine, Pergolide, Pramipexole, Tolcapone, Procyclidine, Trihexyphenidyl, and Benztropine; agents used in the treatment of major depression, including, but not limited to, Amitriptyline, Protriptyline, Desipramine, Nortriptyline, Paroxetine, Fluoxetine, Sertraline, Bupropion, Escitalopram, Mirtazapine, Venlafaxine, Duloxetine; agents used in the treatment of Alzheimer's disease, including, but not limited to, Galanthamine, Tacrine, Donepezil, Rivastigmine, Memantine, Neotropin, Selegiline, Estrogen and Iodoquinol; agents used in the treatment of dementia, including, but not limited to, Thioridazine, Haloperidol, Risperidone, Tacrine, Donepezil, and Rivastigmine; agents used in the treatment of epilepsy, including, but not limited to, Phenyloin, Phenobarbital, Carbamazepine, Valproic acid, Ethosuximide, Gabapentin, Phenobarbital, Solfeton and Felbatol; agents used in the treatment of multiple sclerosis, including, but not limited to, Tolterodine, Oxybutynin, Oxycodone, Interferon $\beta$-1b, Interferon $\beta$-1a, Azathioprine, Methotrexate and Glatiramer; agents used in the treatment of Huntington's disease, including, but not limited to, Amitriptyline, Protriptyline, Desipramine, Nortriptyline, Paroxetine, Fluoxetine, Sertraline, Tetrabenazine, Haloperidol, Chlorpromazine, Thioridazine, Sulpiride, Quetiapine, Clozapine, and Risperidone; agents used in the treatment of diabetes, including, but not limited to, PPAR ligands (e.g., agonists, antagonists, such as Rosiglitazone, Troglitazone and Pioglitazone), insulin secretagogues (e.g., sulfonylurea drugs, such as Glyburide, Glimepiride, Chlorpropamide, Tolbutamide, and Glipizide, and non-sulfonyl secretagogues), $\alpha$-glucosidase inhibitors (e.g., Acarbose, Miglitol, and Voglibose), insulin sensitizers (such as the PPAR-$\gamma$ agonists, e.g., glitazones; biguanides, PTP-1B inhibitors, DPP-IV inhibitors, and 11$\beta$-HSD inhibitors), hepatic glucose output lowering compounds (such as glucagon antagonists and metformin, e.g., Glucophage and Glucophage XR), insulin and insulin derivatives (both long and short acting forms and formulations of insulin); and antiobesity drugs, including, but not limited to, $\beta$-3 agonists, CB-1 agonists, neuropeptide Y5 inhibitors, Ciliary Neurotrophic Factor and derivatives (e.g., Axokine), appetite suppressants (e.g., Sibutramine), and lipase inhibitors (e.g., Orlistat).

The form of administration of concomitant drugs with the crystal of the present invention is not particularly limited and is acceptable as long as the crystal of the present invention is combined with concomitant drugs at the time of administration. Examples of such forms of administration are as follows:

(1) administration of a single formula obtained by simultaneous formulation of the crystal of the present invention with a concomitant drug, (2) simultaneous administration via the same administration route for two kinds of formulas obtained by independent formulations of the crystal of the present invention and a concomitant drug, (3) administrations at different times via the same administration route for two kinds of formulas obtained by independent formulations of the crystal of the present invention and a concomitant drug, (4) simultaneous administration via different administration routes for two kinds of formulas obtained by independent formulations of the crystal of the present invention and a concomitant drug, (5) administrations at different times via different administration routes for two kinds of formulas obtained by independent formulations of the crystal of the present invention and a concomitant drug (e.g., administration in the order of the crystal of the present invention and then a concomitant drug, or administration in the reversed order). These forms of administration are summarized below and abbreviated as a concomitant agent of the present invention.

When administering the concomitant agent of the present invention, a concomitant drug and the crystal of the present invention can be administered at the same time, but the crystal of the present invention can be administered after a concomitant drug is administered or after the crystal of the present invention is administered, a concomitant drug can be administered. When administering at different times, the time difference depends upon the active ingredients to be administered, drug forms and methods of administration. For example, when a concomitant drug is administered first, the crystal of the present invention can be administered within 1 min to 3 days, preferably within 10 min to 1 day and more preferably within 15 min to 1 hour after the concomitant drug is administered. However, if the crystal of the present invention is administered first, a concomitant drug can be administered within 1 min to 1 day, preferably within 10 min to 6 hours and more preferably within 15 min to 1 hour after the crystal of the present invention is administered.

If there are no problems with side effects of the concomitant drugs, any dosages can be set. A daily dosage as a concomitant drug depends upon dosages, administration subjects, administration routes, target diseases, symptoms, etc. For example, in the case of oral administration in patients with schizophrenia (adults, bodyweight of approximately 60 kg), a normal daily dosage ranges from about 0.1 to about 20 mg/kg bodyweight, preferably from about 0.2 to about 10 mg/kg bodyweight and more preferably from about 0.5 to about 10 mg/kg bodyweight. It is preferable that this dosage is administered once daily to several times daily (e.g., 3 times).

If the crystal of the present invention is used in combination with a concomitant drug, the respective dosages can be reduced within a safe range with consideration of the opposite effects of the respective drugs.

The concomitant agent of the present invention exhibits low toxicity. For example, the crystal of the present invention or(and) the aforementioned concomitant drug can be combined with a pharmaceutically acceptable carrier according to the known method to prepare a pharmaceutical composition such as tablets (including sugar-coated tablets and film-coated tablets), powder agents, granular agents, capsules (including soft capsules), liquids, injection solutions, suppositories, sustained-release agents, etc. These compositions can be administered safely orally or non-orally (e.g., including topical, rectal and intravenous routes).

The pharmaceutically acceptable carriers that can be used for manufacturing the concomitant agent of the present invention can be the same as those used in the pharmaceutical composition of the present invention as mentioned above.

A mixing ratio between the crystal of the present invention and a concomitant drug in the concomitant agent of the present invention can be selected appropriately based on the administration subjects, administration routes and diseases.

The aforementioned concomitant drugs can be combined at an appropriate ratio if two or more drugs are combined.

A dosage of the concomitant drug can be selected appropriately based on the dosages used clinically. In addition, a mixing ratio between the crystal of the present invention and a concomitant drug can be selected appropriately based on the administration subjects, administration routes, target diseases, symptoms, combinations, etc. For example, if the administration subject is humans, a concomitant drug can be used in an amount ranging from 0.01 to 100 parts by weight relative to 1 part by weight of the crystal of the present invention.

For example, the content of the crystal of the present invention in the concomitant agent of the present invention varies with the form of formulations. Generally, it is present in a range from about 0.01 to 99.9 wt %, preferably from about 0.1 to 50 wt % and more preferably from about 0.5 to 20 wt % is relative to the entire formula.

The content of a concomitant drug in the concomitant agent of the present invention varies with the form of formulations. Generally it is present in a range from about 0.01 to 99.9 wt %, preferably from about 0.1 to 50 wt % and more preferably from about 0.5 to 20 wt % relative to the entire formula.

The content of an additive such as carriers in the concomitant agent of the present invention varies with the form of formulations. Generally it is present in a range from about 1 to 99.99 wt % and preferably from about 10 to 90 wt % relative to the entire formula.

When the crystal of the present invention and a concomitant drug are formulated independently, the same contents can be applied.

Since the dosages may fluctuate under various conditions as mentioned above, a dosage less than the aforementioned dosages may be sufficient or it may be necessary to administer at a dosage exceeding the range.

EXAMPLES

The present invention is explained in detail by referring to the following Reference Examples, Examples, Formulation Examples, and Experimental Examples. These examples are mere embodiments, which do not limit the present invention, and can be modified within the range not deviating from the scope of the present invention.

The "room temperature" in the following Reference Examples and Examples is generally about 10° C. to about 35° C. % in the yield means mol/mol %, % of solvent used for chromatography means % by volume, and % used for others means wt %. In proton NMR spectrum, OH and NH protons and the like that cannot be identified since they are broad bands are not recorded in the data. In silica gel chromatography, silica gel 60 (230-400 mesh) manufactured by Merk & Co., Inc. was used, and aminopropylsilane-bonded silica gel (Chromatorex NH manufactured by Fuji Silysia Chemical Ltd.) was used for basic silica gel chromatography described as "NH silica gel".

Other abbreviations used in the text mean the following.
s: singlet
d: doublet
dd: doublet of doublets
dt: doublet of triplets
t: triplet
tt: triplet of triplets
td: triplet of doublets
q: quartet
septet: septet
m: multiplet
br: broad
J: coupling constant
Hz: Hertz
CDCl$_3$: deuterated chloroform
DMSO-d$_6$: deuterated dimethyl sulfoxide
$^1$H NMR: proton nuclear magnetic resonance
HPLC: high performance liquid chromatography
THF: tetrahydrofuran
DMF: N,N-dimethylformamide
DMSO: dimethyl sulfoxide
IPE: isopropyl ether
DMA: N,N-dimethylacetamide
DIPEA: N,N-diisopropylethylamine
Pd$_2$(dba)$_3$: tris(dibenzylideneacetone)dipalladium(0)
LC-MS: liquid chromatography-mass spectrometry spectrum
ESI: electrospray-ionization method
API: atmospheric pressure ionization method All reagents and solvents were of commercial quality and used without further purification. The compounds and/or intermediates were purified by preparative high performance liquid chromatography (prep. HPLC) using a Gilson High through Put purification system.

The columns were reversed phase YMC CombiPrep Pro C18, S-5 μm, 19×50 mm. A gradient elution was used (flow rate 20 mL/min), typically starting with 5% acetonitrile/95% water and progressing to 100% acetonitrile over a Period of 7 minutes. All solvents contained 0.1% trifluoroacetic acid (TFA).

Mass spectrometric analysis was performed according to liquid chromatography/mass spectroscopy (LCMS) methods. The method employed a Waters LC-MS System (Agilent HP1100 HPLC and a Micromass ZMD mass spectrometer for the LCMS instrument, a CAPCELL PAK C18, UG120, S-3 μm, 1.5×35 mm for the chromatography column), and a solvent system that was a 5-95% gradient of acetonitrile in water with 0.04% TFA (flow rate 0.5 mL/min; molecular weight range 200-800; cone Voltage 20 V; column temperature 40° C.). All masses were reported as those of the protonated parent ions.

Powder X-ray diffraction analysis was measured using RINT Ultima-IV (manufactured by Rigaku Corporation).

Differential scanning calorimetry (DSC) was measured using a differential scanning calorimeter (DSC1 (manufactured by Mettler-Toledo)) at a temperature rise rate 5° C./min within the range of 25° C. to 240° C.

Heating was performed by Heatblock (manufactured by TAITEC Co., Ltd.).

Reference Example 1-1

Crystal of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (Form A)

a) 3-[4-(benzyloxy)phenyl]-7-methyl-1,3-dihydro-2H-imidazo[4,5-b]pyridin-2-one

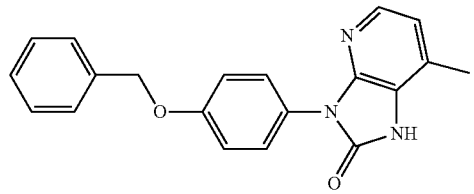 [SMILES: Cc1ccnc2c1[nH]c(=O)n2-c1ccc(OCc2ccccc2)cc1]

A mixture of tert-butyl (2-chloro-4-methylpyridin-3-yl)carbamate (2.00 g), 4-(benzyloxy)aniline hydrochloride (2.91 g), 9,9-dimethyl-4,5-bis(diphenylphosphino)xanthene (381 mg), sodium tert-butoxide (1.90 g) and Pd$_2$(dba)$_3$ (302 mg) in 2-propanol (6 mL) and toluene (24 mL) was stirred under a nitrogen atmosphere at 100° C. for 24 hr. The reaction mixture was concentrated under reduced pressure. The residue was dissolved in methanol, and the precipitates were filtered off. The filtrate was concentrated, and the residue was purified by column chromatography (NH silica gel, eluted with 15%-50% ethyl acetate in hexane) to give 3-[4-(benzyloxy)phenyl]-7-methyl-1,3-dihydro-2H-imidazo[4,5-b]pyridin-2-one (988 mg) as a colorless solid.

MS (API+): [M+H]$^+$ 332.3.

$^1$H NMR (300 MHz, CDCl$_3$) δ 2.39 (3H, s), 5.12 (2H, s), 6.87 (1H, d, J=5.3 Hz), 7.12 (2H, d, J=9.0 Hz), 7.28-7.50 (5H, m), 7.57 (2H, d, J=8.7 Hz), 7.96 (1H, d, J=5.3 Hz), 9.93 (1H, brs).

b) 3-[4-(benzyloxy)phenyl]-1-ethyl-7-methyl-1,3-dihydro-2H-imidazo[4,5-b]pyridin-2-one

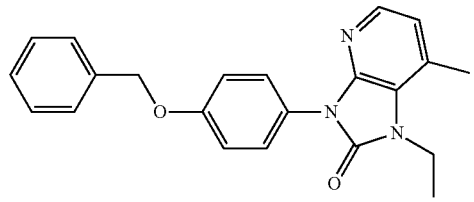 [SMILES: CCn1c(=O)n(-c2ccc(OCc3ccccc3)cc2)c2nccc(C)c21]

Iodoethane (0.289 mL) was added to a mixture of 3-[4-(benzyloxy)phenyl]-7-methyl-1,3-dihydro-2H-imidazo[4,5-b]pyridin-2-one (998 mg) and cesium carbonate (1.96 g) in DMF (10 mL) at room temperature. The mixture was stirred at 50° C. for 4 hr. The mixture was diluted with water at room temperature, and the mixture was extracted with ethyl acetate. The organic layer was separated, washed with water and brine, dried over magnesium sulfate, and then concentrated under reduced pressure. The residue was purified by column chromatography (silica gel, eluted with 15%-30% ethyl acetate in hexane) to give 3-[4-(benzyloxy)phenyl]-1-ethyl-7-methyl-1,3-dihydro-2H-imidazo[4,5-b]pyridin-2-one (801 mg) as a white solid.

MS (API+): [M+H]$^+$ 360.4.

¹H NMR (300 MHz, CDCl₃) δ 1.41 (3H, t, J=7.2 Hz), 2.61 (3H, s), 4.19 (2H, q, J=7.2 Hz), 5.11 (2H, s), 6.81 (1H, d, J=5.3 Hz), 7.10 (2H, d, J=8.7 Hz), 7.30-7.47 (5H, m), 7.53 (2H, d, J=9.1 Hz), 7.91 (1H, d, J=5.3 Hz).

c)  1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one

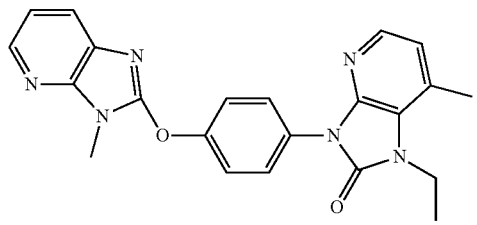 [SMILES: CCn1c(=O)n(-c2ccc(Oc3nc4cccnc4n3C)cc2)c2nccc(C)c21]

A mixture of 3-[4-(benzyloxy)phenyl]-1-ethyl-7-methyl-1,3-dihydro-2H-imidazo[4,5-b]pyridin-2-one (800 mg) and 10% Pd—C (118 mg) in ethanol (20 mL) was hydrogenated overnight under a balloon pressure at room temperature. The catalyst was filtered off, and the filtrate was concentrated in vacuo to give 1-ethyl-3-(4-hydroxyphenyl)-7-methyl-1,3-dihydro-2H-imidazo[4,5-b]pyridin-2-one as a colorless solid. To a mixture of this solid and 3-methyl-2-(methylsulfonyl)-3H-imidazo[4,5-b]pyridine (480 mg) in DMF (10 mL) was added 60% sodium hydride (58.9 mg) at 100° C. The mixture was heated under microwave irradiation at 180° C. for 30 min. The reaction mixture was diluted with methanol and concentrated in vacuo. The residue was purified by column chromatography (NH silica gel, eluted with 30%-50% ethyl acetate in hexane, and silica gel, eluted with 15%-30% ethyl acetate in hexane). The crude substance was purified by HPLC(C18, eluted with water/acetonitrile containing 0.1% trifluoroacetic acid). To the obtained solution was added aqueous saturated sodium hydrogen carbonate, and the mixture was extracted with ethyl acetate. The extract was dried over magnesium sulfate, and then concentrated in vacuo to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (119 mg) as colorless crystals (Form A).

MS (API+): [M+H]⁺ 401.3.

Reference Example 1-2

Crystal of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (Form A)

a)  1-ethyl-3-(4-hydroxyphenyl)-7-methyl-1,3-dihydro-2H-imidazo[4,5-b]pyridin-2-one

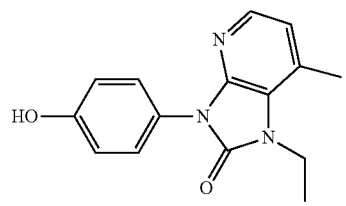 [SMILES: CCn1c(=O)n(-c2ccc(O)cc2)c2nccc(C)c21]

A mixture of 3-[4-(benzyloxy)phenyl]-1-ethyl-7-methyl-1,3-dihydro-2H-imidazo[4,5-b]pyridin-2-one (21.4 g) and 10% Pd—C (3.17 g) in ethanol (400 mL) was hydrogenated under a balloon pressure at room temperature for 2 hr. The catalyst was filtered off, and the filtrate was concentrated in vacuo. The solid was washed with THF-hexane to give 1-ethyl-3-(4-hydroxyphenyl)-7-methyl-1,3-dihydro-2H-imidazo[4,5-b]pyridin-2-one (10.90 g) as a solid.

MS (API+): [M+H]⁺ 270.4.

b)  1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one

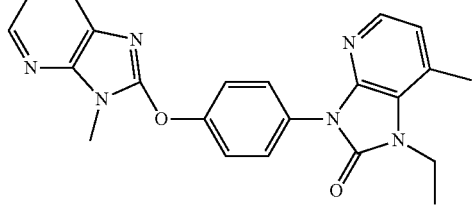

To a solution of 3-methyl-2-(methylsulfonyl)-3H-imidazo[4,5-b]pyridine (1.0 g) and 1-ethyl-3-(4-hydroxyphenyl)-7-methyl-1,3-dihydro-2H-imidazo[4,5-b]pyridin-2-one (1.3 g) in DMF (10 mL) was added 60% sodium hydride (0.23 g) at room temperature, and the mixture was stirred under microwave irradiation at 180° C. for 30 min. To the mixture was added ethanol (10 mL). The formed crystals were collected by filtration, and washed with ethanol. This microwave reaction was repeated two additional times using the same amount of starting materials. The combined crystals were recrystallized from ethanol containing 5% distilled water (270 ml) and dried under reduced pressure to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (3.3 g) as white crystals (Form A).

MS (API+): [M+H]⁺ 401.3.

¹H NMR (300 MHz, DMSO-d₆) δ 1.32 (3H, t, J=7.2 Hz), 2.61 (3H, s), 3.77 (3H, s), 4.12 (2H, q, J=7.2 Hz), 7.00 (1H, d, J=5.7 Hz), 7.20 (1H, dd, J=7.9, 4.9 Hz), 7.58-7.66 (2H, m), 7.71-7.78 (2H, m), 7.80 (1H, dd, J=7.9, 1.1 Hz), 7.87 (1H, d, J=4.9 Hz), 8.22 (1H, dd, J=4.9, 1.5 Hz).

Anal. Calcd for $C_{22}H_{20}N_6O_2$: C, 65.99; H, 5.03; N, 20.99. Found: C, 65.76; H, 5.07; N, 20.85.

The measurement results of powder X-ray diffraction of Form A crystals obtained in Reference Example 1-1 are shown in the following Table 1 and FIG. 1.

TABLE 1

Powder X-ray diffraction data (Form A crystals)

| 2θ (°) | d value (Å) | relative intensity (%) |
|---|---|---|
| 7.88 | 11.2103 | 5 |
| 9.5 | 9.302 | 26 |
| 10.9 | 8.1102 | 38 |
| 14.06 | 6.2937 | 8 |
| 14.58 | 6.0704 | 11 |
| 15.74 | 5.6255 | 67 |
| 16.14 | 5.487 | 22 |
| 16.76 | 5.2854 | 10 |
| 18.3 | 4.8439 | 81 |
| 19.6 | 4.5255 | 6 |
| 20.3 | 4.371 | 61 |
| 21.22 | 4.1835 | 6 |
| 21.84 | 4.0661 | 12 |
| 22.3 | 3.9833 | 10 |
| 22.76 | 3.9038 | 14 |

TABLE 1-continued

Powder X-ray diffraction data (Form A crystals)

| 2θ (°) | d value (Å) | relative intensity (%) |
|---|---|---|
| 23.72 | 3.7479 | 19 |
| 24.68 | 3.6043 | 58 |
| 25.36 | 3.5092 | 23 |
| 26.32 | 3.3833 | 11 |
| 27.1 | 3.2877 | 6 |
| 27.7 | 3.2178 | 100 |
| 28.36 | 3.1444 | 12 |
| 29.94 | 2.982 | 3 |
| 30.48 | 2.9304 | 3 |
| 30.9 | 2.8915 | 5 |
| 31.7 | 2.8203 | 5 |
| 32.84 | 2.725 | 3 |
| 33.14 | 2.701 | 3 |
| 33.94 | 2.6391 | 4 |

Reference Example 2

Crystal of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (Form B)

The crystals of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (Form A) (20 mg, 0.05 mmol) obtained in Reference Example 1-1 were mixed with acetonitrile (3 mL), and dissolved at an inside temperature of 60° C. This solution was filtered through a filter with 0.22 μm pore size, and cooled to 0-5° C. with stirring. The mixture was stirred for 8 hr in a cooled state at 0-5° C. The crystals were collected by filtration to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (crystals of Form B).

Figure 2:
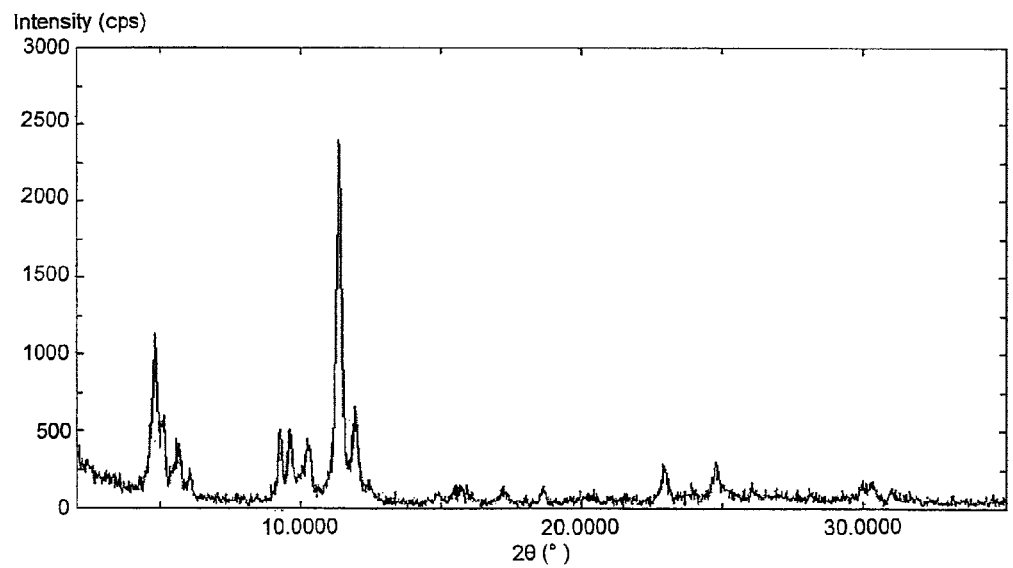
FIG. 2 shows a powder X-ray diffraction pattern of the crystal of Reference Example 2.

The measurement results of powder X-ray diffraction of is the obtained crystals are shown in the following Table 2 and FIG. 2.

TABLE 2

Powder X-ray diffraction data (Form B crystals)

| 2θ (°) | d value (Å) | relative intensity (%) |
|---|---|---|
| 4.82 | 18.3182 | 37 |
| 5.12 | 17.2455 | 19 |
| 5.6 | 15.7684 | 12 |
| 5.7 | 15.492 | 11 |
| 6.08 | 14.5245 | 7 |
| 9.26 | 9.5425 | 20 |
| 9.62 | 9.1862 | 17 |
| 10.22 | 8.6482 | 13 |
| 11.34 | 7.7965 | 96 |
| 11.36 | 7.7828 | 100 |
| 11.92 | 7.4184 | 23 |
| 15.7 | 5.6398 | 5 |
| 15.9 | 5.5693 | 5 |
| 17.18 | 5.1571 | 4 |
| 18.64 | 4.7563 | 6 |
| 22.88 | 3.8836 | 12 |
| 24.58 | 3.6187 | 7 |
| 24.72 | 3.5985 | 11 |
| 25 | 3.5589 | 5 |
| 26.02 | 3.4216 | 6 |
| 29.86 | 2.9898 | 6 |
| 29.98 | 2.9781 | 6 |
| 30.1 | 2.9665 | 5 |
| 30.26 | 2.9512 | 7 |

Reference Example 3

Crystal of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (Form D)

The crystals of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (Form A) (20 mg, 0.05 mmol) obtained in Reference Example 1-1 were mixed with trifluoroethanol (0.5 mL) and dissolved at room temperature. Trifluoroethanol was evaporated under a nitrogen stream while cooling to 0-5° C. The crystals were collected by filtration to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (crystals of Form D).

Figure 3:
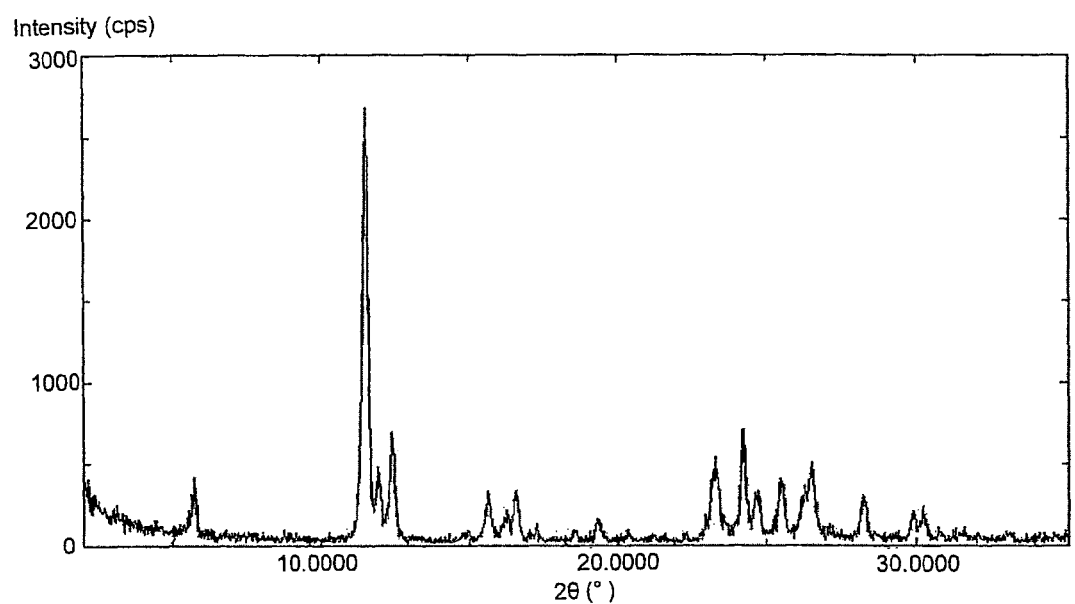
FIG. 3 shows a powder X-ray diffraction pattern of the crystal of Reference Example 3.

The measurement results of powder X-ray diffraction of the obtained crystals are shown in the following Table 3 and FIG. 3.

TABLE 3

Powder X-ray diffraction data (Form D crystals)

| 2θ (°) | d value (Å) | relative intensity (%) |
|---|---|---|
| 5.72 | 15.4378 | 12 |
| 11.52 | 7.675 | 100 |
| 11.96 | 7.3937 | 13 |
| 12.4 | 7.1323 | 24 |
| 15.62 | 5.6685 | 14 |
| 16.26 | 5.4468 | 8 |
| 16.52 | 5.3616 | 11 |
| 19.28 | 4.5999 | 7 |
| 23.26 | 3.821 | 18 |
| 24.18 | 3.6777 | 29 |
| 24.56 | 3.6216 | 11 |
| 24.68 | 3.6043 | 10 |
| 25.54 | 3.4848 | 10 |
| 26.28 | 3.3884 | 13 |
| 26.5 | 3.3607 | 18 |
| 28.14 | 3.1685 | 10 |
| 29.82 | 2.9937 | 8 |
| 29.92 | 2.9839 | 7 |
| 30.2 | 2.9569 | 9 |
| 31.18 | 2.8661 | 4 |

Reference Example 4

Crystal of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (Form E)

The crystals of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (Form A) (20 mg, 0.05 mmol) obtained in Reference Example 1-1 were mixed with acetone (4 mL) and dissolved at inside temperature 50° C. This solution was filtered through a filter with 0.22 μm pore size, water (3 mL) heated to 50° C. was added, and cooled to 0-5° C. with stirring. The mixture was stirred for 8 hr in a cooled state at 0-5° C. The crystals were collected by filtration to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (crystals of Form E).

Figure 4:
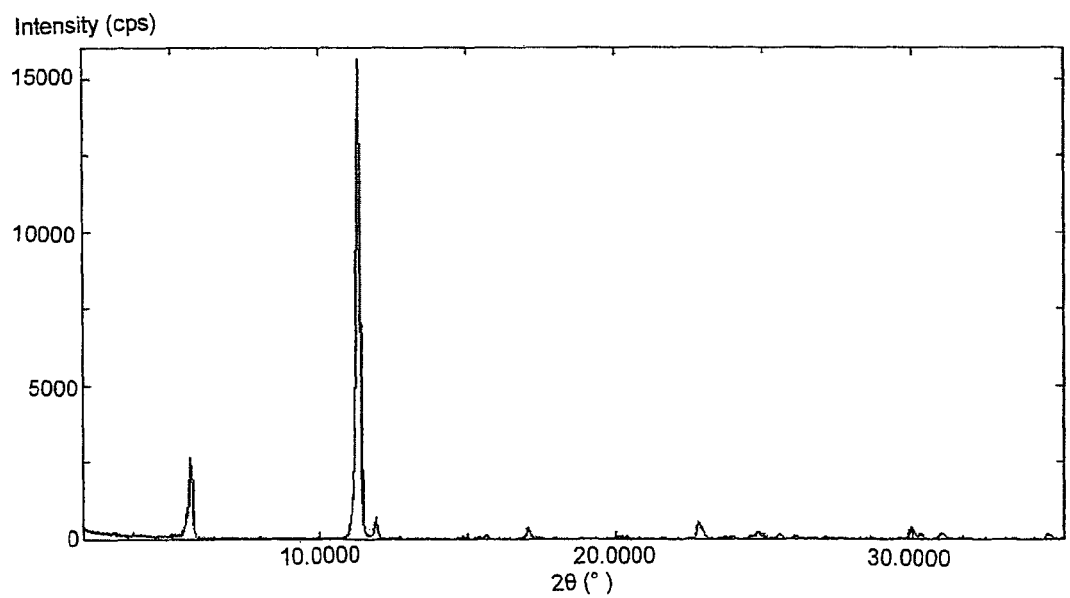
FIG. 4 shows a powder X-ray diffraction pattern of the crystal of Reference Example 4.

The measurement results of powder X-ray diffraction of the obtained crystals are shown in the following Table 4 and FIG. 4.

TABLE 4

| Powder X-ray diffraction data (Form E crystals) | | |
|---|---|---|
| 2θ (°) | d value (Å) | relative intensity (%) |
| 5.64 | 15.6566 | 15 |
| 11.32 | 7.8102 | 100 |
| 11.9 | 7.4308 | 4 |
| 15.4 | 5.749 | 1 |
| 17.02 | 5.2052 | 3 |
| 20.06 | 4.4227 | 1 |
| 20.32 | 4.3667 | 1 |
| 22.76 | 3.9038 | 4 |
| 23.92 | 3.7171 | 1 |
| 24.5 | 3.6304 | 1 |
| 25.52 | 3.4875 | 2 |
| 26.04 | 3.419 | 1 |
| 28.6 | 3.1186 | 1 |
| 29.96 | 2.98 | 3 |
| 30.26 | 2.9512 | 2 |
| 30.9 | 2.8915 | 2 |
| 34.48 | 2.599 | 2 |

Reference Example 5

Crystal of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (Form F)

The crystals of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (Form A) (20 mg, 0.05 mmol) obtained in Reference Example 1-1 were mixed with 2-propanol (10 mL) and dissolved at inside temperature 60° C. This solution was filtered through a filter with 0.22 µm pore size, n-heptane (10 mL) heated to 60° C. was added, and cooled to 0-5° C. with stirring. The mixture was stirred for 8 hr in a is cooled state at 0-5° C. The crystals were collected by filtration to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (crystals of Form F).

Figure 5:
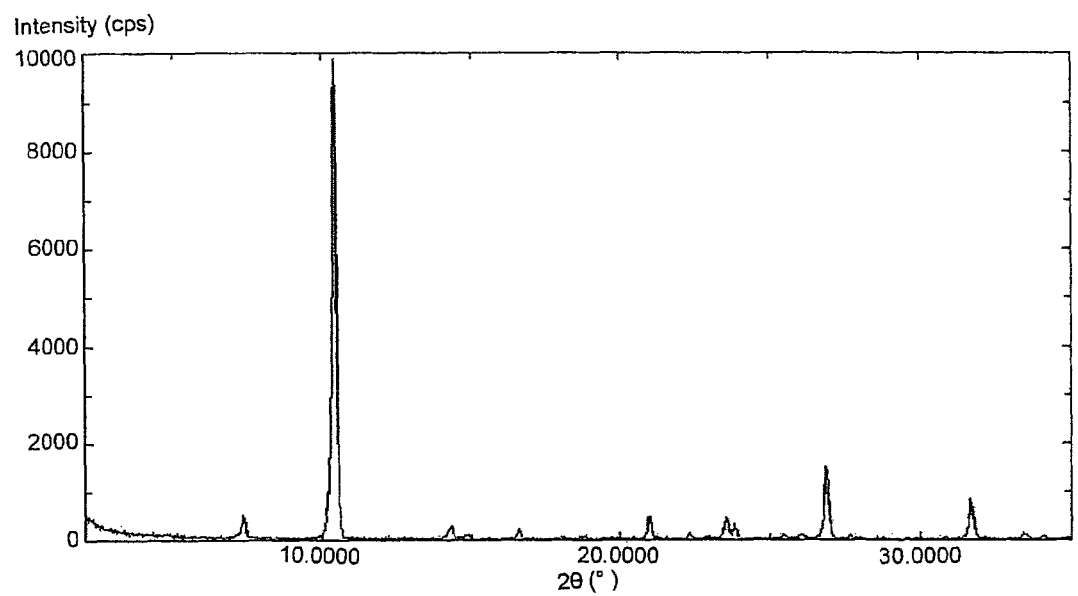
FIG. 5 shows a powder X-ray diffraction pattern of the crystal of Reference Example 5.

The measurement results of powder X-ray diffraction of the obtained crystals are shown in the following Table 5 and FIG. 5.

TABLE 5

| Powder X-ray diffraction data (Form F crystals) | | |
|---|---|---|
| 2θ (°) | d value (Å) | relative intensity (%) |
| 7.38 | 11.9687 | 5 |
| 10.42 | 8.4827 | 100 |
| 14.32 | 6.18 | 3 |
| 14.86 | 5.9566 | 2 |
| 16.56 | 5.3488 | 3 |
| 20.92 | 4.2428 | 6 |
| 20.98 | 4.2308 | 5 |
| 22.28 | 3.9868 | 2 |
| 23.5 | 3.7825 | 6 |
| 23.78 | 3.7386 | 4 |
| 25.5 | 3.4902 | 2 |
| 25.98 | 3.4268 | 2 |
| 26.82 | 3.3214 | 18 |
| 27.62 | 3.2269 | 2 |
| 31.66 | 2.8238 | 12 |
| 33.44 | 2.6774 | 2 |

Reference Example 6

Crystal of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one variable hydrate (Form H)

The crystals of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (Form A) (20 mg, 0.05 mmol) obtained in Reference Example 1-1 were mixed with acetonitrile/water (9:1) (1 mL) and the mixture was stirred at room temperature for a week. The crystals were collected by filtration to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one variable hydrate (water content of the variable hydrate varied within the range of about 4-about 14 wt %) (crystals of Form H).

Figure 6:
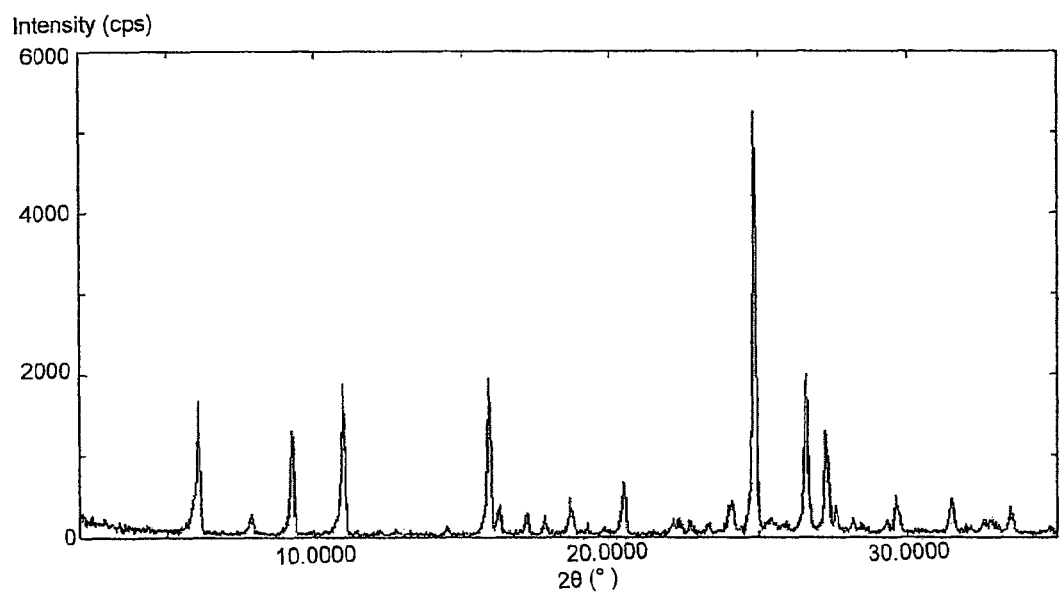
FIG. 6 shows a powder X-ray diffraction pattern of the crystal of Reference Example 6.

The measurement results of powder X-ray diffraction of the obtained crystals are shown in the following Table 6 and FIG. 6.

TABLE 6

| Powder X-ray diffraction data (Form H crystals) | | |
|---|---|---|
| 2θ (°) | d value (Å) | relative intensity (%) |
| 6.06 | 14.5724 | 23 |
| 7.9 | 11.182 | 4 |
| 9.24 | 9.5631 | 18 |
| 10.96 | 8.0659 | 28 |
| 15.86 | 5.5832 | 29 |
| 16.2 | 5.4668 | 5 |
| 17.14 | 5.1691 | 5 |
| 17.76 | 4.99 | 4 |
| 18.62 | 4.7614 | 9 |
| 20.42 | 4.3456 | 12 |
| 24.04 | 3.6988 | 8 |
| 24.8 | 3.5871 | 100 |
| 26.54 | 3.3558 | 29 |
| 27.2 | 3.2758 | 24 |
| 27.54 | 3.2361 | 6 |
| 29.28 | 3.0477 | 3 |
| 29.6 | 3.0154 | 9 |
| 31.46 | 2.8413 | 6 |
| 33.48 | 2.6743 | 5 |

Reference Example 7

Crystal of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one monohydrate (Form I)

The crystals of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (Form A) (20 mg, 0.05 mmol) obtained in Reference Example 1-1 were mixed with ethanol/water (9:1) (1 mL) and the mixture was stirred at room temperature for a week. The crystals were collected by filtration to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one monohydrate (crystals of Form I).

Figure 7:
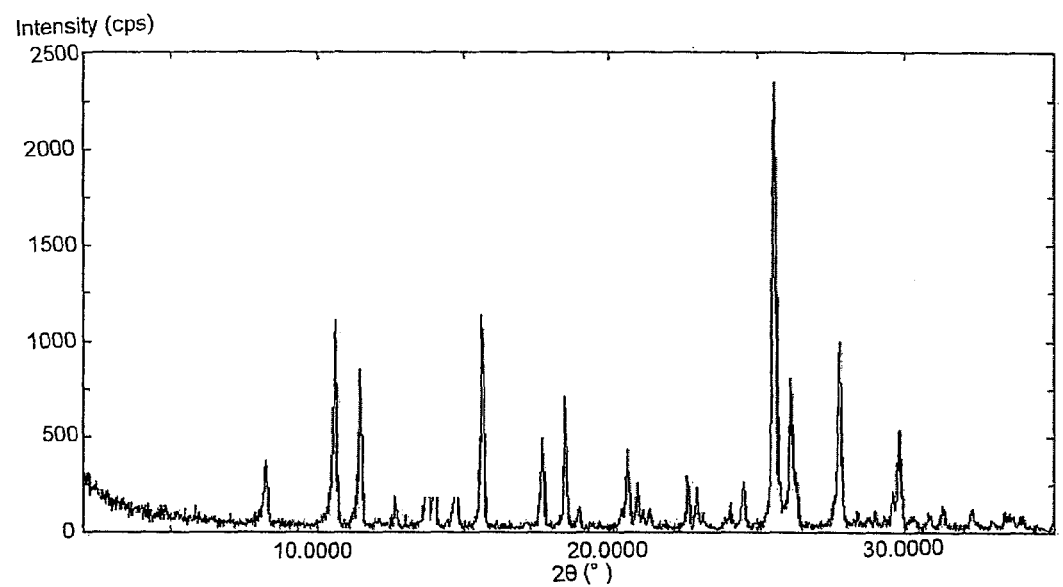
FIG. 7 shows a powder X-ray diffraction pattern of the crystal of Reference Example 7.

The measurement results of powder X-ray diffraction of the obtained crystals are shown in the following Table 7 and FIG. 7.

TABLE 7

Powder X-ray diffraction data (Form I crystals)

| 2θ (°) | d value (Å) | relative intensity (%) |
|---|---|---|
| 8.24 | 10.7213 | 11 |
| 10.6 | 8.339 | 41 |
| 11.44 | 7.7285 | 33 |
| 12.64 | 6.9974 | 5 |
| 13.72 | 6.4489 | 17 |
| 13.94 | 6.3476 | 12 |
| 14.7 | 6.0211 | 16 |
| 15.64 | 5.6613 | 50 |
| 17.68 | 5.0124 | 20 |
| 18.46 | 4.8023 | 31 |
| 18.96 | 4.6768 | 6 |
| 20.62 | 4.3039 | 19 |
| 20.92 | 4.2428 | 6 |
| 22.62 | 3.9277 | 12 |
| 22.92 | 3.8769 | 8 |
| 23.16 | 3.8373 | 5 |
| 24.5 | 3.6304 | 10 |
| 25.52 | 3.4875 | 100 |
| 26.1 | 3.4113 | 37 |
| 27.72 | 3.2155 | 42 |
| 29.6 | 3.0154 | 8 |
| 29.78 | 2.9976 | 22 |

Example 1

Crystal of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (Form G)

(1) The crystals of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (Form A: 100 mg) were dissolved in ethanol (20 mL) at 80° C., and the solution was allowed to cool to room temperature. The mixture was stirred at room temperature for 350 hr. The solids were collected by filtration to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (50 mg) as crystals (Form G).

(2) The crystals of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (Form A: 40.0 g) were dissolved in DMSO (400 mL) at 95° C., and the solution was allowed to cool to 85° C. To the solution was slowly added ethanol (400 mL) at 85° C., and the mixture was allowed to cool to 80° C. To the solution was added a seed crystal (Form G, 50 mg) at 80° C. The mixture was stirred and maintained at 73° C. for 20 hr. The solids were collected by filtration, and washed with ethanol (500 mL) to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (19.5 g) as white crystals (Form G).

Example 2

Crystal of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (Form G)

The crystals of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (Form A: 600 mg) were stirred in ethanol (60 mL) at room temperature for 168 hr. The solids were collected by filtration to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (350 mg) as crystals (Form G).

MS (API+): [M+H]$^+$ 401.1.

$^1$H NMR (400 MHz, DMSO-d$_6$) δ 1.25-1.38 (3H, m), 2.61 (3H, s), 3.78 (3H, s), 4.04-4.18 (2H, m), 6.96-7.04 (1H, m), 7.17-7.25 (1H, m), 7.59-7.66 (2H, m), 7.71-7.77 (2H, m), 7.78-7.83 (1H, m), 7.85-7.91 (1H, m), 8.16-8.28 (1H, m).

Anal. Calcd for C$_{22}$H$_{20}$N$_6$O$_2$: C, 65.99; H, 5.03; N, 20.99. Found: C, 65.73; H, 5.12; N, 20.85.

Example 3

Crystal of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (Form G)

The crystals (3.0 g) of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one obtained in Example 7a) were dissolved in DMSO (33 mL) at 90° C. To the solution was slowly added ethanol (30 mL) at 80-90° C. The crystal (Form G) obtained in Example 2 was added as a seed crystal at 80-90° C. The mixture was stirred at 60-65° C. for 6 hr, and at room temperature for 18 hr. The solids were collected by filtration, and washed with ethanol (15 mL) to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (1.3 g) as white crystals (Form G).

Example 4

Crystal of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (Form G)

The crystals (3.0 g) of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one obtained in Example 7a) were dissolved in DMSO (33 mL) at 90-95° C. To the solution was slowly added ethyl acetate (30 mL) at 70-90° C. The crystal (Form G) obtained in Example 3 was added as a seed crystal at 80-90° C. The mixture was stirred at 45-50° C. for 25 min and at 70-75° C. for 3 hr. The mixture was cooled to 0-5° C., and stirred for 1 hr. The solids were collected by filtration and washed with ethyl acetate (15 mL) to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (2.6 g) as crystals (Form G).

Example 5

Crystal of 1-ethyl-7-methyl-3-{4-[(3-methyl-3H-imidazo[4.5-b]pyridin-2-yl)oxy]phenyl}-1,3-dihydro-2H-imidazo[4,5-b]pyridin-2-one (Form G)

A solution of 3-methyl-2-(methylsulfonyl)-3H-imidazo[4,5-b]pyridine (20.4 g, 96.55 mmol) in DMA (117 mL) was added to a solution of 1-ethyl-3-(4-hydroxyphenyl)-7-methyl-1,3-dihydro-2H-imidazo[4,5-b]pyridin-2-one (26.0 g, 96.55 mmol) and potassium tert-butoxide (11.4 g) in DMA (96 mL) at room temperature. The mixture was stirred at 95-100° C. for 1.5 hr. Water (221 mL) was added at 80-100° C. The precipitates were collected at room temperature and dried under reduced pressure to give 1-ethyl- 7-methyl-3-{4-[(3-methyl-3H-imidazo[4,5-b]pyridin-2-yl) oxy]phenyl}-1,3-dihydro-2H-imidazo[4,5-b]pyridin-2-one (35.8 g) as a crude product.

The crude 1-ethyl-7-methyl-3-{4-[(3-methyl-3H-imidazo [4,5-b]pyridin-2-yl)oxy]phenyl}-1,3-dihydro-2H-imidazo [4,5-b]pyridin-2-one (10.0 g) was dissolved in DMSO (150 mL) at 90-100° C. The solution was filtered through a paper filter, and washed with DMSO (10 mL). The combined filtrate was slowly added to a mixture of the crystals (Form G: 100 mg) (as a seed crystal) obtained in Example 4 in ethyl acetate (100 mL) at 5-30° C. The mixture was stirred at room temperature for 17 hr and at 70° C. for 1 hr. The mixture was slowly cooled to 25° C. and stirred for 2 hr. The mixture was stirred at 0-10° C. for 1 hr, and at room temperature for 1 hr. The solids were collected by filtration, and dried under reduced pressure at 50° C. to give 1-ethyl-7-methyl-3-{4-[(3-methyl-3H-imidazo[4,5-b]pyridin-2-yl)oxy]phenyl}-1, 3-dihydro-2H-imidazo[4,5-b]pyridin-2-one (8.0 g) as white crystals (Form G).

Example 6

Crystal of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (Form G)

A solution of 3-methyl-2-(methylsulfonyl)-3H-imidazo [4,5-b]pyridine (40.8 g, 193.09 mmol) in DMA (234 mL) was added to a solution of 1-ethyl-3-(4-hydroxyphenyl)-7-methyl-1,3-dihydro-2H-imidazo[4,5-b]pyridin-2-one (52.0 g, 193.09 mmol) and potassium tert-butoxide (22.8 g) in DMA (192 mL) at room temperature. The mixture was stirred at 90-100° C. for 1 hr. Water (442 mL) was added at 80-100° C. The precipitates were collected at room temperature and dried under reduced pressure to give 1-ethyl-7-methyl-3-{4-[(3-methyl-3H-imidazo[4,5-b]pyridin-2-yl) oxy]phenyl}-1,3-dihydro-2H-imidazo[4,5-b]pyridin-2-one (72.4 g) as a crude product.

The crude 1-ethyl-7-methyl-3-{4-[(3-methyl-3H-imidazo [4,5-b]pyridin-2-yl)oxy]phenyl}-1,3-dihydro-2H-imidazo [4,5-b]pyridin-2-one (60.0 g) was dissolved in DMSO (900 mL) at 90-100° C. The solution was filtered through a paper filter, and washed with DMSO (60 mL). The combined filtrate was slowly added to a mixture of the crystals (Form G: 600 mg) (as a seed crystal) obtained in Example 5 in ethyl acetate (600 mL) at 0-30° C. The mixture was stirred at 70° C. for 0.5 hr and cooled to room temperature. The mixture was stirred at room temperature for 1 hr, at 0-10° C. for 1 hr, and at room temperature for 1 hr. The solids were collected by filtration, and dried under reduced pressure at 50° C. to give 1-ethyl-7-methyl-3-{4-[(3-methyl-3H-imidazo[4,5-b] pyridin-2-yl)oxy]phenyl}-1,3-dihydro-2H-imidazo[4,5-b] pyridin-2-one (47.9 g) as white crystals (Form G).

MS (ESI+): [M+H]$^+$ 401.2.

$^1$H NMR (500 MHz, CDCl$_3$) δ 1.42 (3H, t), 2.62 (3H, s), 3.84 (3H, s), 4.15-4.27 (2H, m), 6.81-6.92 (1H, m), 7.10-7.18 (1H, m), 7.52-7.61 (2H, m), 7.73-7.80 (1H, m), 7.82-7.87 (2H, m), 7.91-7.95 (1H, m), 8.20-8.29 (1H, m).

Example 7

Crystal of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (Form G)

a) A solution of 3-methyl-2-(methylsulfonyl)-3H-imidazo[4, 5-b]pyridine (78.4 g, 371.33 mmol) in DMA (420 mL) was added to a solution of 1-ethyl-3-(4-hydroxyphenyl)-7-methyl-1,3-dihydro-2H-imidazo[4,5-b]pyridin-2-one (100.0 g, 371.33 mmol) and potassium tert-butoxide (51.5 g) in DMA (370 mL) at room temperature. The mixture was stirred at 90-100° C. for 1 hr. Water (780 mL) was added at 90-100° C. The precipitates were collected at room temperature and dried under reduced pressure to give 1-ethyl-7-methyl-3-{4-[(3-methyl-3H-imidazo[4,5b] pyridin-2-yl)oxy]phenyl}-1,3-dihydro-2H-imidazo[4,5-b]pyridin-2-one (127.7 g) as crystals. The obtained crystals (125.0 g) were dissolved in DMSO (1375 mL) at 90-95° C. To the solution was slowly added ethanol (1250 mL) at 80-95° C., and the mixture was allowed to cool to room temperature. The solids were collected by filtration, washed with ethanol (625 mL) to give 1-ethyl-7-methyl-3-{4-[(3-methyl-3H-imidazo[4,5-b]pyridin-2-yl)oxy] phenyl}-1,3-dihydro-2H-imidazo[4,5-b]pyridin-2-one (103.9 g) as crystals.

b) A mixture of the obtained crystals (55.0 g) in a solution of DMSO (275 mL) and ethanol (275 mL) was stirred at 70-75° C. for 0.5 hr, and the mixture was allowed to cool to room temperature. The solids were collected by filtration, and washed with ethanol (165 mL) to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (52.2 g) as crystals. The obtained crystals (5.0 g) were dissolved in DMSO (50 mL) at 95° C. The solution was filtered through a paper filter and washed with DMSO (5 mL). To the combined filtrate was slowly added ethanol (50 mL) at 73-95° C. To the solution were added the crystals obtained in Example 4 (Form G: 5 mg) as a seed crystal at 73° C. The mixture was allowed to cool to room temperature. The mixture was stirred at 70-75° C. for 7 hr, and allowed to cool to room temperature. The mixture was stirred at 70-75° C. for 8 hr, and cooled to room temperature. The mixture was stirred at 70-75° C. for 2 hr, and the mixture was stirred at room temperature for 1 hr, and 0-10° C. for 1 hr. The solids were collected by filtration, and dried under reduced pressure at 50° C. to give 1-ethyl-7-methyl-3-{4-[(3-methyl-3H-imidazo[4,5-b]pyridin-2-yl)oxy]phenyl}-1,3-dihydro-2H-imidazo[4, 5-b]pyridin-2-one (4.5 g) as white crystals (Form G).

Example 8

Crystal of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (Form G)

3-Methyl-2-(methylsulfonyl)-3H-imidazo[4,5-b]pyridine (8.62 g, 40.8 mmol) was added to a mixture of 1-ethyl-3-(4-hydroxyphenyl)-7-methyl-1,3-dihydro-2H-imidazo[4,5-b]pyridin-2-one (10.0 g, 37.1 mmol), potassium carbonate (6.15 g) and water (4.25 mL) in DMA (75 mL) at room temperature. The mixture was stirred at 80-90° C. for 1 hr. Water (135 mL) was added at 45° C. The precipitates were collected at room temperature, and dried under reduced pressure to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (14.13 g) as a crude product.

The crude 1-ethyl-7-methyl-3-{4-[(3-methyl-3H-imidazo [4,5-b]pyridin-2-yl)oxy]phenyl}-1,3-dihydro-2H-imidazo [4,5-b]pyridin-2-one (12.0 g) was dissolved in DMSO (228 mL) at 90° C. The solution was filtered through glass filter. The filtrate was heated to 90° C. and stirred at 30° C. for 1 hr. Ethanol (72 mL) was added and the mixture was stirred for 1 hr. After stirring at 60° C. for 4.5 hr, the mixture was cooled to room temperature. After stirring at 10° C. for 4.5 hr, the precipitates were collected and dried under reduced pressure to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (10.32 g) as white crystals (Form G).

Example 9

Crystal of 1-ethyl-7-methyl-3-{4-[(3-methyl-3H-imidazo[4,5-b]pyridin-2-yl)oxy]phenyl}-1,3-dihydro-2H-imidazo[4,5b]pyridin-2-one (Form G)

3-Methyl-2-(methylsulfonyl)-3H-imidazo[4,5-b]pyridine (258.9 g, 1.22 mmol) was added to a mixture of 1-ethyl-3-(4-hydroxyphenyl)-7-methyl-1,3-dihydro-2H-imidazo[4,5-b]pyridin-2-one (300.0 g, 1.11 mmol), potassium carbonate (184.7 g) and water (127.5 mL) in DMA (1950 mL) at room temperature. DMA (300 mL) was further added and the mixture was stirred at 86-87° C. for 1 hr. Water (4050 mL) was added at 45° C. The precipitates were collected at 25° C., and dried under reduced pressure to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (435.87 g) as a crude product.

The crude 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (400.0 g) was dissolved in DMSO (7600 mL) at 80-90° C. The solution was filtered through a glass filter. The filtrate was heated to 80-90° C., and the crystals (Form G: 4 g) obtained in Example 8 were added to the solution at 50° C. as a seed crystal. After cooling to 30° C., ethanol (2400 mL) was added. The mixture was heated to 60-70° C. and cooled to room temperature. After stirring under ice-cooling, the precipitates were collected and dried under reduced pressure to give 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (344.04 g) as white crystals (Form G).

Figure 8:
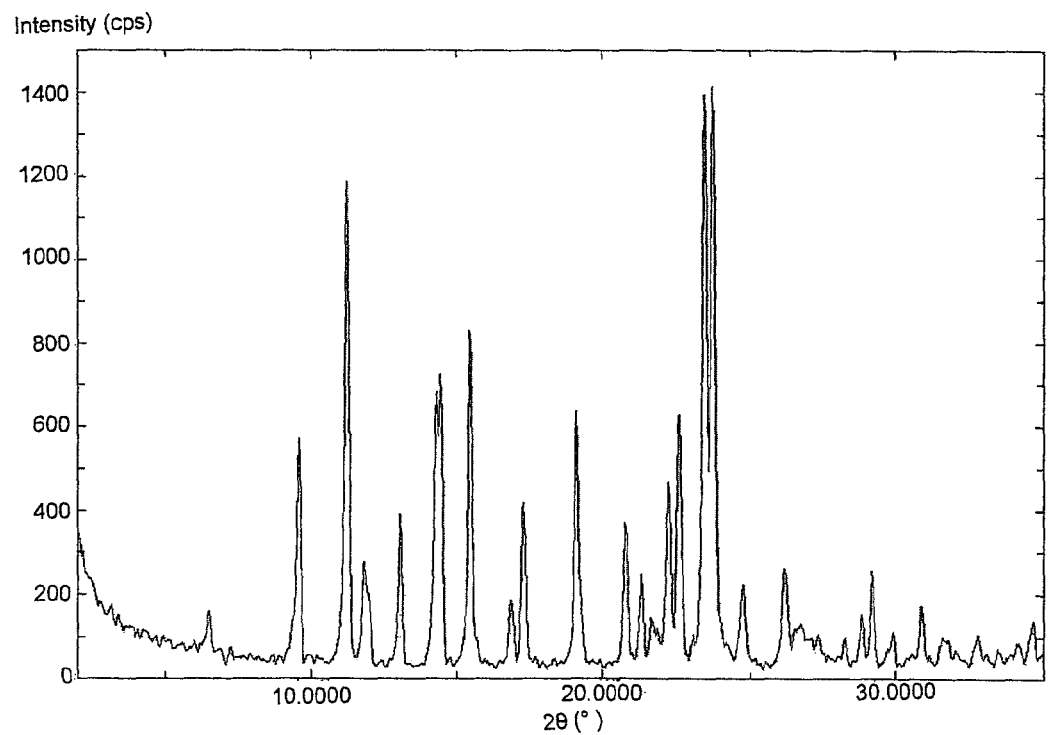
FIG. 8 shows a powder X-ray diffraction pattern of the crystal of Example 1(2).
Figure 9:
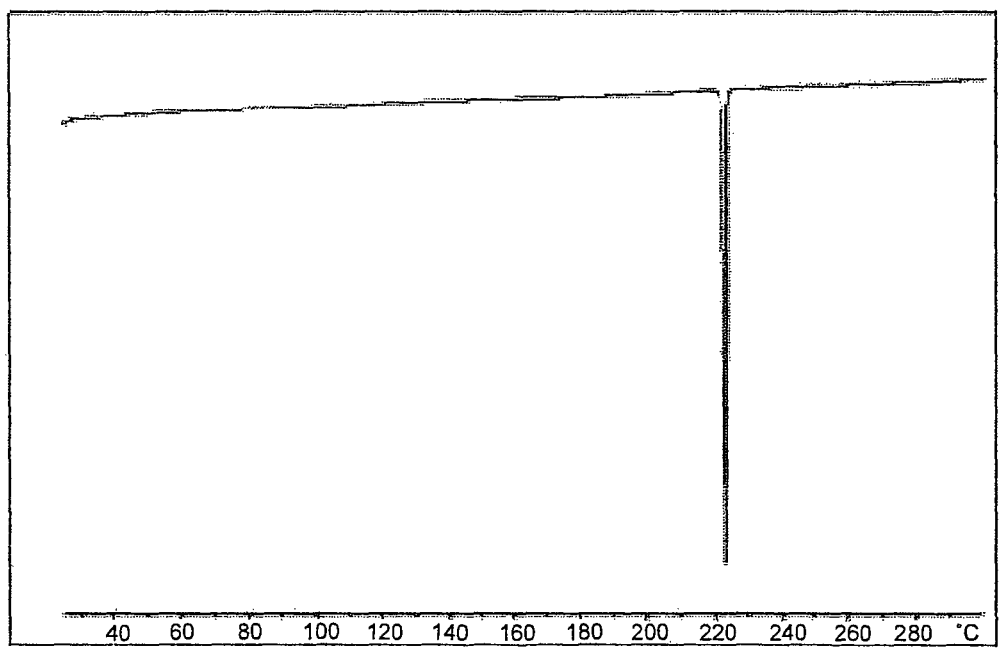
FIG. 9 shows DSC thermoanalytical data of the crystal of Example 1(2).

The measurement results of powder X-ray diffraction of the Form G crystals obtained in Example 1(2) are shown in the following Table 8 and FIG. 8. In addition, the DSC thermoanalytical data of the crystals are shown in FIG. 9.

TABLE 8

| Powder X-ray diffraction data (Form G crystals) | | |
|---|---|---|
| 2θ (°) | d value (Å) | relative intensity (%) |
| 6.5 | 13.5869 | 8 |
| 9.58 | 9.2245 | 38 |
| 11.22 | 7.8796 | 82 |
| 11.82 | 7.4809 | 17 |
| 13.08 | 6.763 | 25 |
| 14.26 | 6.2059 | 47 |
| 14.44 | 6.1289 | 49 |
| 15.46 | 5.7268 | 58 |
| 16.9 | 5.2419 | 12 |
| 17.28 | 5.1275 | 29 |
| 19.12 | 4.638 | 45 |
| 20.8 | 4.267 | 25 |
| 21.32 | 4.1641 | 16 |
| 21.88 | 4.0588 | 5 |
| 22.24 | 3.9939 | 30 |
| 22.58 | 3.9345 | 44 |
| 23.44 | 3.7921 | 100 |
| 23.27 | 3.7479 | 100 |
| 24.74 | 3.5957 | 15 |
| 26.12 | 3.4088 | 17 |
| 28.24 | 3.1575 | 5 |

TABLE 8-continued

| Powder X-ray diffraction data (Form G crystals) | | |
|---|---|---|
| 2θ (°) | d value (Å) | relative intensity (%) |
| 28.82 | 3.0953 | 10 |
| 29.18 | 3.0579 | 20 |
| 30.88 | 2.8933 | 13 |
| 31.64 | 2.8255 | 6 |
| 32.78 | 2.7298 | 7 |
| 34.68 | 2.5845 | 7 |

Formulation Example 1

| (1) Crystal of Example 1 | 10.0 g |
|---|---|
| (2) Lactose | 70.0 g |
| (3) Cornstarch | 50.0 g |
| (4) Soluble starch | 7.0 g |
| (5) Magnesium stearate | 3.0 g |

After 10.0 g of the crystal of Example 1 and 3.0 g of magnesium stearate are granulated in 70 mL of aqueous solution of soluble starch (7.0 g as soluble starch) and then dried, the resulting mixture is mixed with 70.0 g of lactose and 50.0 g of cornstarch (lactose, cornstarch, soluble starch and magnesium stearate are all products in compliance with Japanese Pharmacopoeia). The mixture is compressed to obtain a tablet.

Experimental Example 1

Study of Crystallization from Various Solvents

The crystals of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (Form A) (20 mg, 0.05 mmol) obtained in Reference Example 1-1 were maintained at 55° C., and various solvents were added until almost the whole amount was dissolved. This solution was filtered through a filter with 0.22 μm pore size, and cooled to 0-5° C. with stirring. The mixture was stirred for 8 hr under cooling at 0-5° C. The crystals of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one formed were collected by filtration, and the crystal form of the crystalline products was confirmed. The results are shown in Table 9.

TABLE 9

| solvent | solubility at 55° C. (mg/mL) | crystal form |
|---|---|---|
| methanol | 5.6 | Form A |
| ethanol | 2.6 | Form A |
| 2-propanol | <2.7 | Form A |
| acetone | 6.5 | Form A |
| methylethylketone | 6.8 | Form A |
| ethyl acetate | 3.4 | Form A |
| acetonitrile | 8.1 | Form B |
| toluene | 5.2 | Form G |
| chloroform | >200 | Form A |
| tetrahydrofuran | 26 | Form A |
| trifluoroethanol | >200 | Form D |

As shown above, in the crystallization from various solvents, Form A crystals were preferentially crystallized, and Form G crystals were crystallized only under the toluene condition where use for the production of a drug substance for pharmaceutical products is limited from the aspect of residual solvent.

Experimental Example 2

Solvent Suspending Test of Crystal Form Mixture

Crystal form mixtures containing the same weight of each crystal form of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one obtained in Reference Examples 1-1, 3 and 4, and Example 1 were prepared to the total amount of 20 mg. The crystal form mixtures were mixed with ethanol (1 mL), and the mixtures were stirred at room temperature. After stirring for one week, and after stirring for 2 weeks, the crystals of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one formed were collected by filtration, and the crystal form of the crystalline products was confirmed. The results are shown in Table 10.

TABLE 10

| | crystal form | |
|---|---|---|
| crystal form mixture | 1 week later | 2 weeks later |
| Form A + Form G | Form G | Form G |
| Form A + Form E | Form A + Form G | Form G |
| Form A + Form D + Form E + Form G | Form G | Form G |

As shown above, the mixtures of various crystal forms transformed into Form G crystal 2 weeks later at room temperature and under suspending in ethanol. The results have clarified that the crystal (Form G) of the present invention is thermodynamically stable under suspending in ethanol at m room temperature.

Experimental Example 3

Solvent Suspending Test of Form A Crystal in Various Solvents

The crystals of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (Form A) (20 mg, 0.05 mmol) obtained in Reference Example 1-1 were mixed with various solvents (1 mL) and the mixture was stirred at room temperature. After stirring for one week, and after stirring for 2 weeks, the crystals of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one formed were collected by filtration, and the crystal form of the crystalline products was confirmed. The results are shown in Table 11.

TABLE 11

| | crystal form | |
|---|---|---|
| solvent | 1 week later | 2 weeks later |
| methanol | Form G | Form G |
| isopropyl alcohol | Form A | Form A |
| acetone | Form G | Form G |
| methylethylketone | Form G | Form G |
| ethyl acetate | Form A + Form G | Form G |
| toluene | Form G | Form G |

TABLE 11-continued

| | crystal form | |
|---|---|---|
| solvent | 1 week later | 2 weeks later |
| tetrahydrofuran | Form G | Form G |
| 1-butanol | Form A | Form A |

As shown above, Form A crystal was transformed into Form G crystal when suspended in many of the solvents. The results have revealed that the crystal (Form G) of the present invention is thermodynamically more stable when suspended in various solvents at room temperature than Form A preferentially obtained by crystallization from a solution.

Experimental Example 4

Preservation Stability Test

The crystals of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one (Form G, 5-10 mg) obtained in Example 1 were placed in a glass bottle, sealed with a metal cap and preserved at 80° C. The sample was taken out 1 week and 2 weeks later, dissolved in a water/acetonitrile mixed solution at a concentration of 0.2 mg/mL and analogs were measured by Alliance HPLC 2695 (Waters Corporation). The results are shown in Table 12.

TABLE 12

| storage condition | appearance | area percentage (%) of HPLC peak area of main form | crystal form |
|---|---|---|---|
| prestorage | white crystalline powder | 99.7 | Form G |
| 80° C., 1 week | no change | 99.7 | Form G |
| 80° C., 2 weeks | no change | 99.6 | Form G |

From the above-mentioned results, it has been clarified that the crystal (Form G) of the present invention has very high chemical and physical stability.

Experimental Example 5

PDE Enzyme Inhibition

Human PDE10A enzyme was generated from Sf9 or COS-7 cells transfected with the full-length gene. The cloned enzyme was extracted from homogenized cell pellets. The extracted enzyme from Sf9 cells was partially purified using His-tag affinity column. The enzyme was stored at −70° C. until use. PDE activity was measured using an SPA (Scintillation Proximity Assay) (GE Healthcare). To evaluate the inhibitory activity, 10 μL of serially diluted 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one was incubated with 20 μL of PDE enzyme in an assay buffer (50 mM HEPES-NaOH, 8.3 mM $MgCl_2$, 1.7 mM EGTA, 0.1% BSA (pH 7.4)) for 30 min at room temperature. The final concentration of DMSO in the assay was 1 percent as compounds were tested in duplicate in 96-well half-area plates (Corning). To start the reaction, 10 μL of substrate [$^3$H] cGMP (25 or 50 nM; enclosed in SPA kits from GE Healthcare or purchased from PerkinElmer, respectively) was added to a final assay volume of 40 μL. After 60 min of incubation at room temperature, yttrium SPA beads containing zinc sulphate were added (6 mg/mL, 20 μL) to terminate the PDE reaction. After standing still for 60 min, the assay plates were counted on a scintillation counter (PerkinElmer) and the inhibition rate was calculated. The inhibition rate was calculated based on the control wells containing DMSO as 0% and control wells without enzyme as 100%. The results are shown in Table 13.

TABLE 13

| Inhibition rate (%) (10 μM) | Inhibition rate (%) (1 μM) |
|---|---|
| 106 | 109 |

INDUSTRIAL APPLICABILITY

Since the crystal of the present invention shows a superior PDE10A inhibitory action, it can provide a prophylactic or therapeutic drug clinically useful for a disease such as schizophrenia and the like. In addition, since the crystal of the present invention is superior in the efficacy, low toxicity, stability, in vivo kinetics etc. (particularly, stability), it is useful as a medicament.

While some of the embodiments of the present invention have been described in detail in the above, it is, however, possible for those of ordinary skill in the art to make various modifications and changes to the particular embodiments shown without substantially departing from the teaching and advantages of the present invention. Such modifications and changes are encompassed in the spirit and scope of the present invention as set forth in the appended claims.

This application is based on patent application No. 2011-138920 filed in Japan, the contents of which are incorporated in full herein by this reference.

The invention claimed is:

1. A crystal of 1-ethyl-7-methyl-3-{4-[(3-methyl-3H-imidazo[4,5-b]pyridin-2-yl)oxy]phenyl}-1,3-dihydro-2H-imidazo[4,5-b]pyridin-2-one showing an X-ray powder diffraction pattern having characteristic peaks at interplaner spacings (d) of 13.59±0.2, 9.22±0.2, 7.88±0.2, 7.48±0.2, 6.76±0.2, 6.21±0.2, 6.13±0.2, 5.73±0.2, 5.24±0.2, 5.13±0.2, 4.64±0.2, 4.27±0.2, 4.16±0.2, 4.06±0.2, 3.99±0.2, 3.93±0.2, 3.79±0.2, 3.75±0.2, 3.60±0.2, 3.41±0.2, 3.16±0.2, 3.10±0.2, 3.06±0.2, 2.89±0.2, 2.83±0.2, 2.73±0.2 and 2.58±0.2 Angstroms in powder X-ray diffraction.

2. The crystal according to claim 1, which shows an initial temperature of about 222- about 224° C. of an endothermic behavior caused by melting in DSC measurement (temperature increase rate 5° C./min).

3. A pharmaceutical composition comprising the crystal according to claim 1, and a pharmacologically acceptable carrier.

4. A method of treating schizophrenia in a mammal, comprising administering an effective amount of the crystal according to claim 1 to the mammal.

* * * * *